US009039974B2

(12) United States Patent
Hironaka et al.

(10) Patent No.: US 9,039,974 B2
(45) Date of Patent: May 26, 2015

(54) BIOLOGICAL SAMPLE MEASURING DEVICE

(75) Inventors: Shouko Hironaka, Ehime (JP); Teppei Shinno, Ehime (JP); Eriko Yoshioka, Ehime (JP); Takashi Miki, Ehime (JP)

(73) Assignee: PANASONIC HEALTHCARE HOLDINGS CO., LTD., Tokyo (JP)

( * ) Notice: Subject to any disclaimer, the term of this patent is extended or adjusted under 35 U.S.C. 154(b) by 0 days.

(21) Appl. No.: 13/993,171

(22) PCT Filed: Jan. 16, 2012

(86) PCT No.: PCT/JP2012/000204
§ 371 (c)(1),
(2), (4) Date: Jun. 11, 2013

(87) PCT Pub. No.: WO2012/105165
PCT Pub. Date: Aug. 9, 2012

(65) Prior Publication Data
US 2013/0266482 A1    Oct. 10, 2013

(30) Foreign Application Priority Data

Feb. 2, 2011    (JP) .................. 2011-020728

(51) Int. Cl.
*G01N 27/00*      (2006.01)
*G01N 27/04*      (2006.01)
(Continued)

(52) U.S. Cl.
CPC ............ *G01N 33/66* (2013.01); *G01N 27/3273* (2013.01); *G01N 27/3271* (2013.01)

(58) Field of Classification Search
USPC ........ 205/77–794.555; 422/50–98; 436/8–19, 436/86–99
See application file for complete search history.

(56) References Cited

U.S. PATENT DOCUMENTS

| 5,354,447 A | 10/1994 | Uenoyama et al. |
| 6,824,670 B2 | 11/2004 | Tokunaga et al. |

(Continued)

FOREIGN PATENT DOCUMENTS

| GB | 2 254 436 | 10/1992 |
| JP | 2-6737 | 1/1990 |

(Continued)

OTHER PUBLICATIONS

International Search Report issued Feb. 28, 2012 in International (PCT) Application No. PCT/JP2012/000204.

*Primary Examiner* — Paul Hyun
*Assistant Examiner* — Robert Eom
(74) *Attorney, Agent, or Firm* — Wenderoth, Lind & Ponack, L.L.P.

(57) ABSTRACT

A biological sample measuring device including a mounting portion to which a biological sample measuring sensor is mounted, a voltage application section that applies voltage to a counter electrode of the biological sample measuring sensor mounted to the mounting portion, amplifiers that are selectively connected to a working electrode of the biological sample measuring sensor, and a determination section that is connected to these amplifiers. The determination section has a threshold determination section that determines a voltage value obtained by voltage conversion of the current value of the working electrode, a same determination section that selectively connects the amplifiers to the working electrode depending on the determination of the threshold determination section, and identifies the sample deposited on the biological sample measuring sensor from the output of the selected amplifier, and an output section that outputs a measurement value corresponding to the identified sample.

6 Claims, 20 Drawing Sheets

(51) Int. Cl.
*G01N 33/66* (2006.01)
*G01N 27/327* (2006.01)

(56) References Cited

U.S. PATENT DOCUMENTS

| | | |
|---|---|---|
| 7,083,712 B2 | 8/2006 | Morita et al. |
| 7,122,111 B2 | 10/2006 | Tokunaga et al. |
| 2002/0139692 A1 | 10/2002 | Tokunaga et al. |
| 2004/0235178 A1 | 11/2004 | Tokunaga et al. |
| 2005/0000829 A1 | 1/2005 | Morita et al. |
| 2006/0231423 A1* | 10/2006 | Harding et al. ............... 205/792 |

FOREIGN PATENT DOCUMENTS

| | | |
|---|---|---|
| JP | 5-164724 | 6/1993 |
| JP | 6-506144 | 7/1994 |
| JP | 6-294755 | 10/1994 |
| JP | 9-201337 | 8/1997 |
| JP | 2001-153839 | 6/2001 |
| JP | 2002-62341 | 2/2002 |
| JP | 2004-256293 | 9/2004 |
| JP | 2010-71898 | 4/2010 |
| WO | 92/17778 | 10/1992 |
| WO | 03/044514 | 5/2003 |

* cited by examiner

When amplifier 14 was used (5°C)

| Measurement sample | Identification result | |
|---|---|---|
| | Control liquid | Blood |
| Control liquid | 1495 | 5 |
| Blood | 1 | 3999 |

(a)

When amplifier 15 was used (present invention) (5°C)

| Measurement sample | Identification result | |
|---|---|---|
| | Control liquid | Blood |
| Control liquid | 1500 | 0 |
| Blood | 0 | 4000 |

BIOLOGICAL SAMPLE MEASURING DEVICE

TECHNICAL FIELD

The present invention relates to a biological sample measuring device for measuring biological information, such as a blood glucose level.

BACKGROUND ART

Conventional biological sample measuring devices were configured as follows.

Specifically, a conventional biological sample measuring device comprised a mounting portion to which was mounted a biological sample measuring sensor in which a reagent was provided on an electrode section including at least a working electrode and a counter electrode, a voltage application section that applied voltage to an electrode section of the biological sample measuring sensor mounted to the mounting portion, an amplifier connected to the electrode section of the biological sample measuring sensor, a determination section connected to the amplifier, and a controller for controlling the voltage application section, the amplifier, and the determination section.

With a conventional biological sample measuring device, when blood is deposited on the biological sample measuring sensor, the reagent and the blood react, an output current that is outputted from the electrode section according to the blood glucose level is amplified by the amplifier, and the blood glucose level is displayed according to this outputted current value.

Also, to maintain and manage the measurement accuracy of a conventional biological sample measuring device, a control liquid whose blood glucose level, etc., is already known is periodically deposited on the reagent portion, and it is confirmed whether or not the blood glucose level corresponding to the control liquid is correctly displayed.

Thus, with a conventional biological sample measuring device, whether the biological sample deposited on the sensor is blood or control liquid is determined by the determination section according to the output result from the amplifier, the method for calculating the blood glucose level from the output of the amplifier is selected on the basis of this determination result, and the blood glucose level is calculated on the basis of the selected calculation method (see Patent Literature 1, for example).

In other words, a conventional biological sample measuring device takes advantage of the fact that the reaction state of the reagent with respect to blood is different from the reaction state of the reagent with respect to the control liquid, and the determination section thereby determines whether what is deposited on the reagent is blood or a control liquid, and the blood glucose level is calculated on the basis of this determination result.

CITATION LIST

Patent Literature

Patent Literature 1: Japanese Laid-Open Patent Application 2001-153839

SUMMARY

However, the following problems were encountered with the conventional biological sample measuring device discussed above.

Specifically, an advantage to the biological sample measuring device disclosed in the above-mentioned publication is that measurement accuracy can be maintained and managed by using a control liquid. Nevertheless, since the reaction slows down at lower temperatures, it is possible that the signal will be so faint that the control liquid is misidentified as whole blood. Also, the response current value during measurement of biological samples of low concentration ends up being very low, just as in measurement at low temperature, so there is the risk that mistaken values slip through undetected.

Technical Problem

It is an object of the present invention to provide a biological sample measuring device capable of accurate measurement with faint signals.

Solution to Problem

The biological sample measuring device pertaining to the first invention comprises a mounting portion, a voltage application section, first and second amplifiers, and a controller. To the mounting portion is mounted a biological sample measuring sensor on which is deposited a biological sample that reacts with a reagent provided on an electrode section including at least a working electrode and a counter electrode. The voltage application section applies voltage to the electrode section of the biological sample measuring sensor mounted to the mounting portion. The first and second amplifiers are selectively connected to the electrode section of the biological sample measuring sensor, and amplify a signal outputted from the electrode section. The first amplifier amplifies the signal at a first amplitude. The second amplifier amplifies the signal at a second amplitude that is greater than the first amplitude. The controller compares the value of the output signal outputted from the electrode section with a preset threshold, and selectively uses either the first amplifier or the second amplifier.

With a biological sample measuring device in which a biological sample measuring sensor on which blood or another such biological sample is deposited is mounted, voltage is applied, and biological information such as the blood glucose level is measured, this device comprises a plurality of amplifiers (first and second amplifiers) having different degrees of amplification. The controller compares the output value from the electrode section of the biological sample measuring sensor with a specific threshold, and selects and uses one of the amplifiers with different degrees of amplification, according to this comparison result.

The above-mentioned "signal" includes a current value outputted from the electrode section of the biological sample measuring sensor, and a voltage value obtained by voltage conversion of this current.

Consequently, if the value of the output signal is lower than the threshold in a low-temperature environment, for example, a more amplified output value can be obtained by performing switching control of the amplifiers (range switching control) so that the second amplifier with its higher degree of amplification is selected and used. As a result, even in environments of widely varying temperature, the amplifier having the proper degree of amplification can be used for amplification processing, so resolution is improved over that in the past, and more accurate measurement can be performed.

The biological sample measuring device pertaining to the second invention is the biological sample measuring device pertaining to the first invention, wherein the controller determines the type of biological sample on the basis of the output result outputted from either the first amplifier or the second amplifier.

Here, in determining whether the biological sample deposited on the sensor is a blood sample or a control liquid, for example, amplification processing is performed using the amplifier having the proper degree of amplification according to the output signal outputted from the biological sample measuring sensor.

The determination of the type of biological sample mentioned above includes distinguishing between a blood sample and a control liquid, for example. A control liquid is used to adjust the measurement result by using a sample for which the result is already known, in order to maintain the measurement accuracy of the biological sample measuring device.

Consequently, even when determining the type of biological sample in a low-temperature environment, the resolution can be increased and accurate type determination can be accomplished by selecting the amplifier having the proper degree of amplification from among a plurality of amplifiers, according to the value of the outputted signal, and using this amplifier for amplification processing.

The biological sample measuring device pertaining to the third invention is the biological sample measuring device pertaining to the second invention, wherein the controller detects the slope in a specific time band in a graph of the output result, and determines whether the biological sample deposited on the biological sample measuring sensor is a blood sample or a control liquid.

Here, in the above-mentioned determination of the type of biological sample, it is determined whether the sample is a blood sample or a control liquid.

When a blood sample and a control liquid are compared, the control liquid is faster than the blood sample in terms of the speed at which it reacts with the reagent of the biological sample measuring sensor. That is, a control liquid will react with the reagent right away and the output current will peak at an early stage, whereas a blood sample will react more gradually with the reagent and the output current value will peak after a specific amount of time has passed.

With the biological sample measuring device of the present invention, this difference in characteristics between a blood sample and a control liquid is utilized to detect the slope of a graph showing the output value after a specific amount of time has passed, and determine the type of sample.

More specifically, the sample is determined to be blood if the slope of the time band after the elapse of a specific length of time is positive in a graph of the output value, and a control liquid if the slope is negative.

Consequently, resolution can be increased over that in the past, and the type of sample can be determined more accurately, by performing the above-mentioned switching control of the amplifiers.

The biological sample measuring device pertaining to the fourth invention is the biological sample measuring device pertaining to the first invention, wherein the controller measures the concentration of the biological sample on the basis of the output result outputted from the first amplifier or the second amplifier.

Here, the above-mentioned switching control of the amplifiers is utilized in measuring the concentration of the biological sample (such as measuring the blood glucose level).

Consequently, if the signal outputted from the biological sample measuring sensor has a low value, amplification processing can be performed by selecting the amplifier having the greater degree of amplification. As a result, the resolution of the biological sample measuring device can be increased ad blood glucose level or the like can be measured accurately even in low-temperature environments, etc.

The biological sample measuring device pertaining to the fifth invention is the biological sample measuring device pertaining to the fourth invention, wherein the controller selects between the first and second amplifiers by comparing the threshold with the output result of a voltage pattern used for biological sample detection and applied prior to measurement of the concentration of the biological sample.

Here, the above-mentioned amplifier switching control is performed by comparing a specific threshold to the output signal of a voltage application pattern applied for sample detection in the biological sample measuring sensor.

The above-mentioned voltage application pattern used for biological sample detection is the voltage applied for the purpose of detecting whether or not the biological sample deposited on the biological sample measuring sensor has reached the region where the reagent is deposited.

Consequently, switching control of a plurality of amplifiers can be carried out after performing threshold determination by using the output signal for the voltage applied at a stage prior to the start of measurement of the blood glucose level, etc.

Advantageous Effects

With the biological sample measuring device pertaining to the present invention, the output signal from the electrode section is weaker during measurement at low temperatures, so the accuracy of measuring blood glucose level, etc., at lower temperatures is improved over that in the past by selecting the second amplifier, which has a higher degree of amplification than the first amplifier, and outputting the amplified signal.

BRIEF DESCRIPTION OF DRAWINGS

FIG. 9a is a comparative table of the determination results for a control liquid and a blood sample when using a first amplifier (amplifier 14) with a lower degree of amplification in a low-temperature environment, and FIG. 9b is a comparative table of the determination results for a control liquid and a blood sample when using a second amplifier (amplifier 15) with a higher degree of amplification in a low-temperature environment;

DESCRIPTION OF EMBODIMENTS

Embodiment 1

The biological sample measuring device pertaining to an embodiment of the present invention will now be described through reference to FIGS. 1 to 9b.

Configuration of Biological Sample Measuring Device

Figure 1:
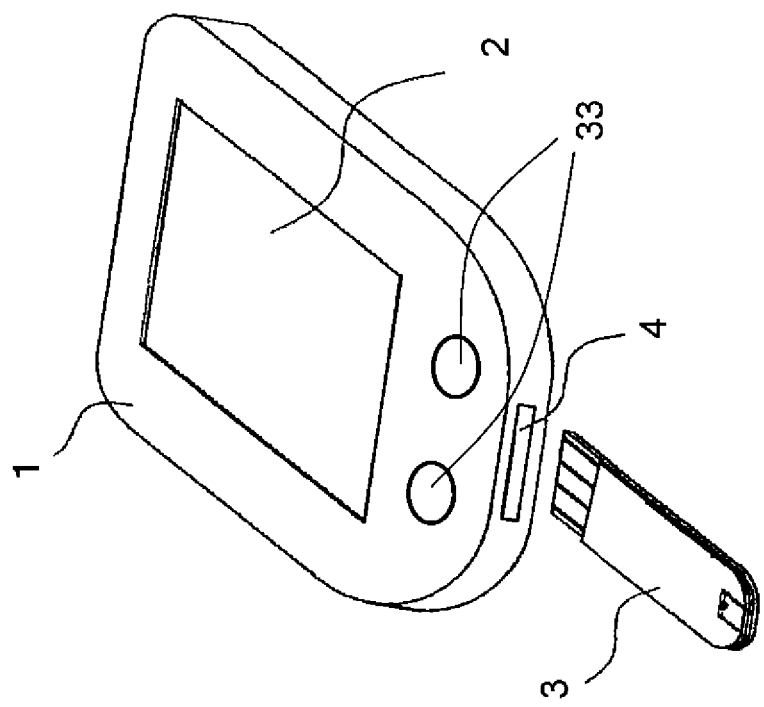
FIG. 1 is an oblique view of the biological sample measuring device pertaining to an embodiment of the present invention.

As shown in FIG. 1, the biological sample measuring device pertaining to this embodiment comprises a main body case 1, a display section 2 provided on the surface of this case, control buttons 33, and a mounting portion 4 for a biological sample measuring sensor 3, provided at the lower end of the main body case 1.

As shown in FIGS. 2a to 2c, the biological sample measuring sensor 3 comprises a substrate 5, a spacer 6, and a cover 7 which are stacked and integrated. FIG. 2a is a developed oblique view of the biological sample measuring sensor 3, FIG. 2b is a cross section of the biological sample measuring sensor 3 as seen from the side, and FIG. 2c is a plan view of the biological sample measuring sensor 3 (showing a state in which there is no cover 7).

A counter electrode 8 and a working electrode 9 included in the electrode section are provided on the substrate 5.

A reagent 10 is provided over the counter electrode 8 and the working electrode 9.

A groove 11 is formed in the spacer 6. A capillary, which is a blood supply channel, is formed by the groove 11, the substrate 5, and the cover 7.

The blood (an example of a biological sample) deposited on the biological sample measuring sensor 3 moves under capillary action through the groove 11 forming the capillary, and upon reaching the portion with the reagent 10, a reaction occurs between the reagent 10 and the glucose in the blood. With the biological sample measuring device in this embodiment, the blood glucose level, etc., is found on the basis of this reaction value.

As shown in FIGS. 2a to 2c, the substrate 5 is longer than the spacer 6 and the cover 7 in the lengthwise direction, and is formed so that the portions of the substrate 5 where the counter electrode 8 and the working electrode 9 are provided (corresponding respectively to portions A and B in FIG. 2c) are exposed. This is so that the electrical circuit in the main body case 1 and the biological sample measuring sensor 3 will be electrically connected when the biological sample measuring sensor 3 has been mounted to the mounting portion 4 of the main body case 1.

Figure 2:
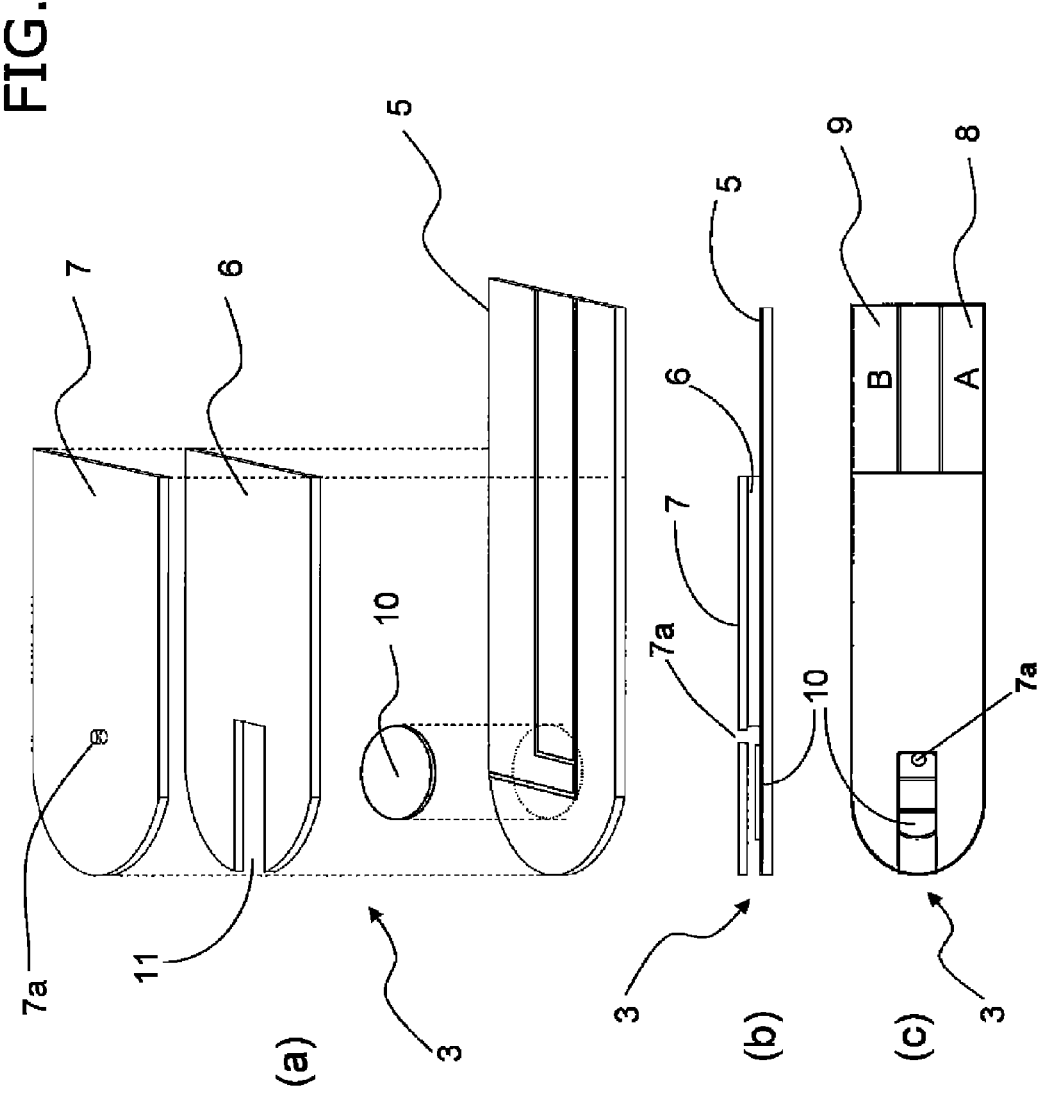
FIG. 2a is an exploded oblique view of the biological sample measuring sensor used in the biological sample measuring device of FIG. 1.
FIG. 2b is a side cross section thereof.
FIG. 2c is a plan view thereof.

An air hole 7a for promoting capillary action within the capillary is provided to the cover 7. As shown in FIG. 2b, the air hole 7a should be disposed further back (to the right in FIG. 2) than the position where the reagent 10 is placed on the biological sample measuring sensor 3. This is so that the blood or the like (biological sample) will be deposited on the distal end side (the left side in FIG. 2) of the capillary, and the blood (biological sample) will be smoothly introduced under capillary action up to the position of the reagent 10.

Figure 3:
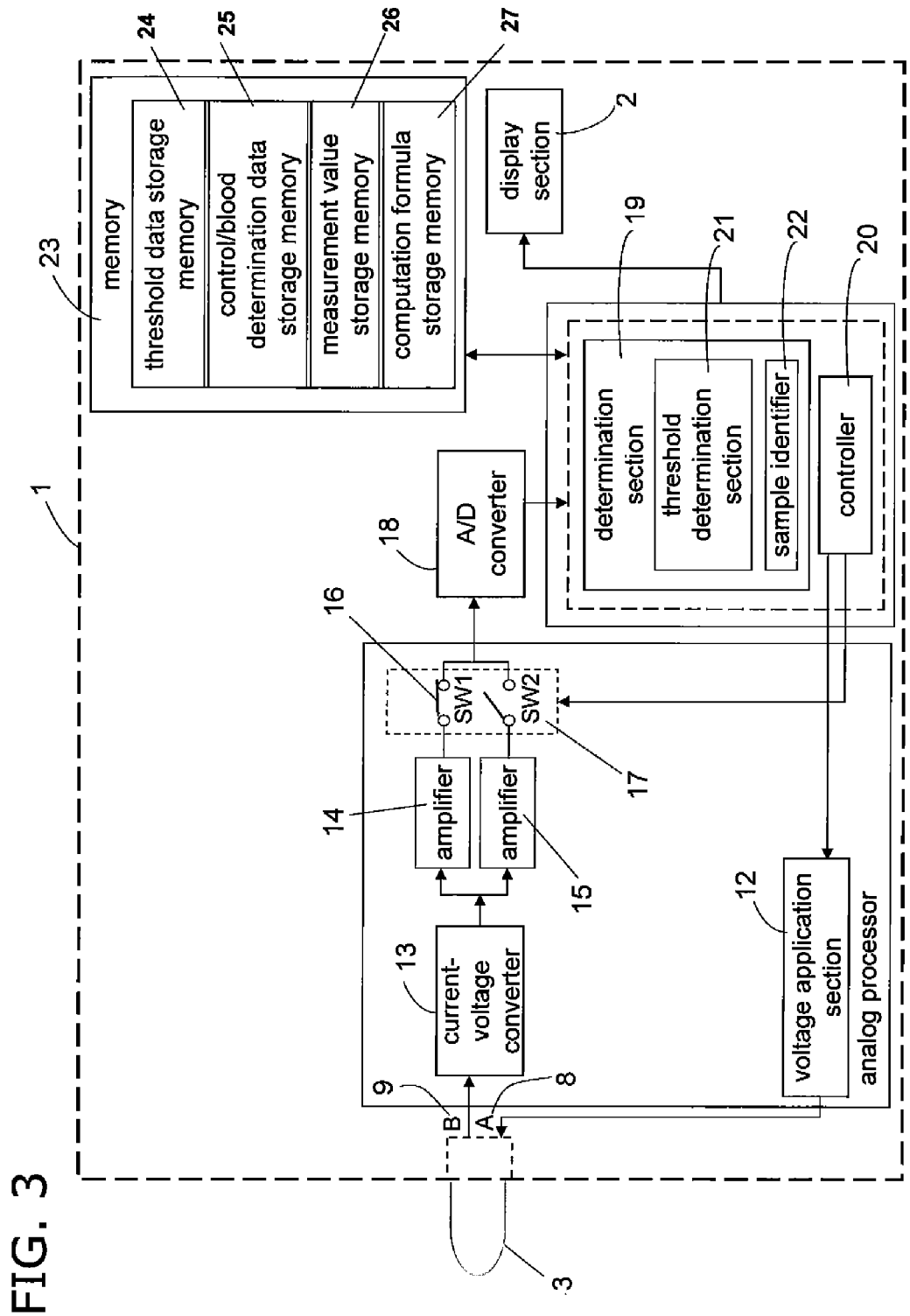
FIG. 3 is a control block diagram of the biological sample measuring device of FIG. 1.

As shown in the control blocks of FIG. 3, the counter electrode 8 is connected to a voltage application section 12. A current-voltage converter 13 is connected to the working electrode 9. The amplifiers 14 and 15 are connected in parallel on the output side of the current-voltage converter 13. The amplifiers 14 and 15 are also connected via switches 16 and 17, respectively, to an A/D converter 18, and perform amplification processing on the side selected by a controller 20 (discussed below).

The amplifier 14 uses a specific degree of amplification (first degree of amplification) to amplify and output a signal (voltage value) received from the current-voltage converter 13. The degree of amplification set for the amplifier 14 is ×1 (5 kΩ), for example.

The amplifier 15 uses a specific degree of amplification (second degree of amplification) that is greater than the degree of amplification (first degree of amplification) set for the amplifier 14 to amplify and output a signal (voltage value) received from the current-voltage converter 13. The degree of amplification set for the amplifier 15 is ×4 (20 kΩ), for example.

The switches 16 and 17 switch the degree of amplification in the amplification processing of the signal obtained from the biological sample measuring sensor 3, by connecting the A/D converter 18 with the amplifier 14 or the amplifier 15, depending on which one was selected by the controller 20 (discussed below). We will assume that at the start of measurement, the switch 16 side is in an ON state and the amplifier 14 and the A/D converter 18 are connected.

Everything from the current-voltage converter 13 to the amplifiers 14 and 15 and the switches 16 and 17 in the biological sample measuring device of this embodiment is an analog processor that processes analog signals.

The A/D converter 18 inputs the signals amplified by the amplifiers 14 and 15 via the switches 16 and 17, and is connected to a determination section (controller) 19.

The determination section 19 is controlled by the controller 20 along with the voltage application section 12, the amplifiers 14 and 15, and the switches 16 and 17. The determination section 19 has a threshold determination section 21, a sample identifier 22, and an output section (not shown). The determination section 19 is connected to a memory 23.

The threshold determination section 21 performs threshold determination by comprising a specific threshold with the output signal that has been converted from a current value into a voltage value by the current-voltage converter 13, then amplified by the amplifier 14 or the amplifier 15, and then converted into a digital signal by the A/D converter 18.

The sample identifier 22 determines the type of biological sample deposited on the biological sample measuring sensor 3 on the basis of the output value of the amplifier 14 or 15 selected connected to the working electrode 9 by the controller 20.

The output section (not shown) outputs a measurement value for the identified biological sample (such as the blood glucose level) to the display section 2.

The memory 23 has a threshold data storage memory 24, a control/blood determination data storage memory 25, a measurement value storage memory 26, a computation formula storage memory 27, and so forth.

The threshold data storage memory 24 holds threshold data used by the threshold determination section 21.

The control/blood determination data storage memory 25 holds data for determining the type of biological sample at the sample identifier 22.

The measurement value storage memory 26 holds values outputted from the output section (not shown) to the display section 2.

The computation formula storage memory 27 holds computation formulas for calculating measurement results for the biological sample, such as the blood glucose level.

Determining the Type of Biological Sample

The determination of the type of biological sample in the biological sample measuring device of this embodiment will be described through reference to FIGS. 4 and 5.

Figure 4:
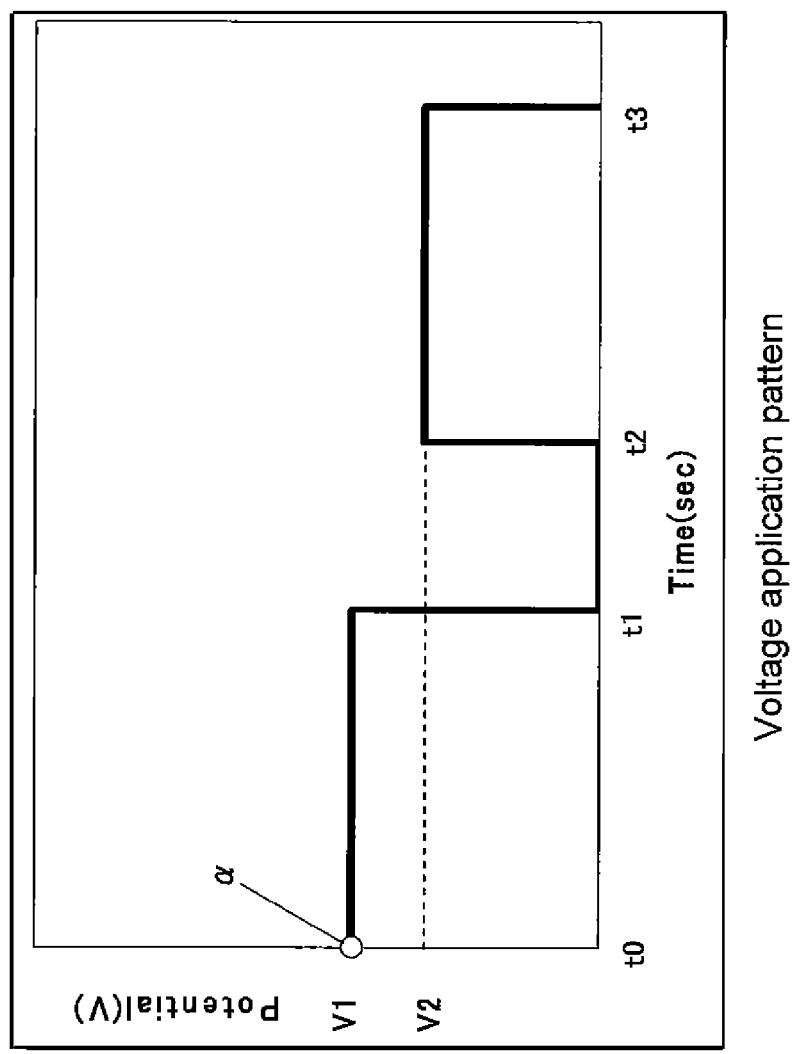
FIG. 4 is a graph of the voltage pattern applied in the biological sample measuring device of FIG. 1.

FIG. 4 shows an example of the voltage application pattern applied from the voltage application section 12 to the counter electrode 8.

In this embodiment, a specific voltage V1 is applied for a time t0-t1 immediately after the start of measurement, after which a specific voltage V2 is applied for a time t2-t3. The above-mentioned specific voltages V1 and V2 are, for example, from 0.05 to 1 V, preferably 0.1 to 0.8 V, and more preferably 0.2 to 0.5 V.

The specific voltage V1 applied for the time t0-t1 is a pre-application voltage that is applied prior to the application of glucose measurement voltage in order to promote the reaction between the blood sample and the reagent. The specific voltage V2 applied for the time t2-t3 is the glucose measurement voltage.

In this embodiment, voltages of different magnitude (V1 and V2) are divided up into two applications. When voltage is applied to the counter electrode 8 in this application pattern, the output current from the working electrode 9 is converted into voltage by the current-voltage converter 13, after which it is inputted through the amplifier 14 or the amplifier 15 to the A/D converter 18. The voltage value shown in FIG. 5 is then outputted from the A/D converter 18 according to the magnitude of this input voltage.

Figure 5:
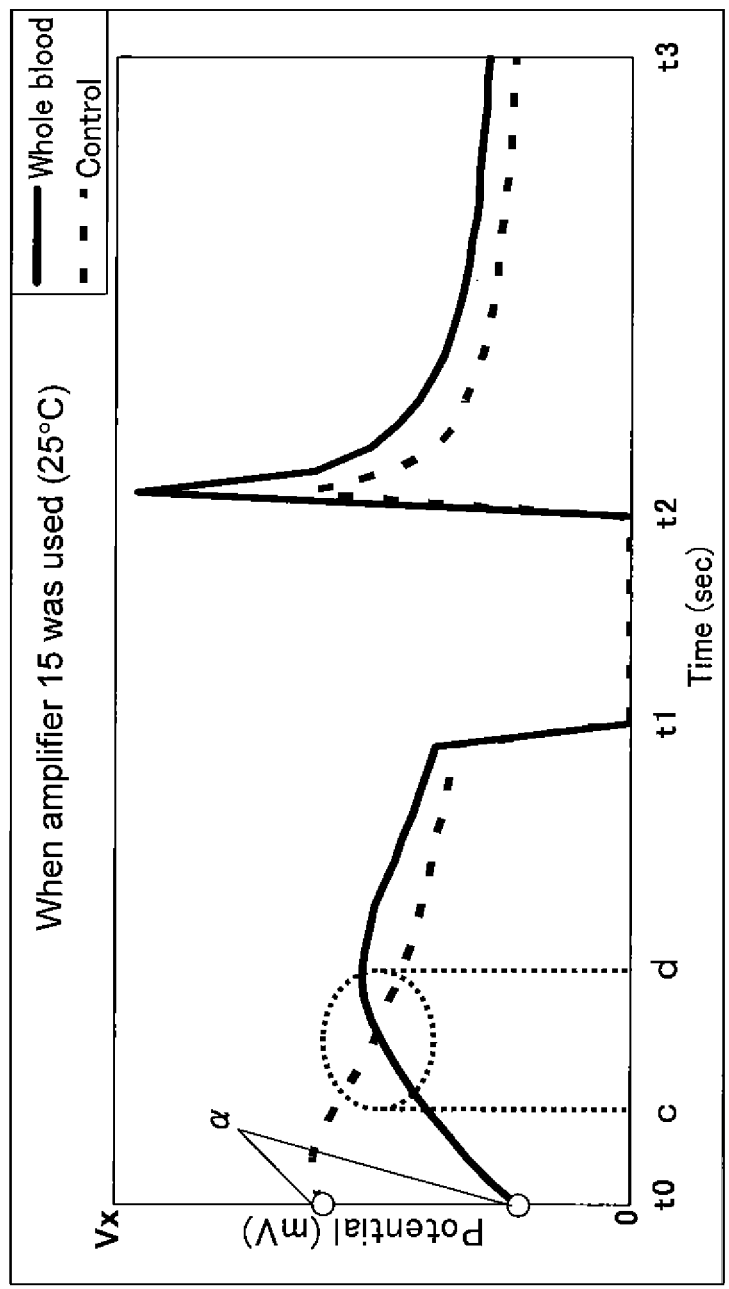
FIG. 5 is an operating waveform diagram in a constant-temperature environment for the biological sample measuring device of FIG. 1.

The output of A/D conversion is a digital value of 8 to 16 bits, with each bit being either "1" or "0." In the graph in FIG. 5, the change over time in this digital value is shown in analog fashion to make the effect of this embodiment easier to comprehend.

In FIG. 5, the solid line is the output when a blood sample was deposited on the biological sample measuring sensor 3, and the broken line is the output when a control liquid was deposited on the biological sample measuring sensor 3.

As shown in FIG. 5, what stands out in this graph is that with a blood sample, the value rises continuously between c and d on the time axis, whereas with a control liquid, the value falls continuously between c and d. The reason behind this behavior is that the reaction between the blood sample and the reagent 10 proceeds gradually, whereas the reaction between the control liquid and the reagent 10 occurs suddenly at the initial stage, and then gradually tapers off between c and d on the time axis, after a specific amount of time has passed.

With the biological sample measuring device in this embodiment, the change in the output voltage value between c and d on the time axis in the graph shown in FIG. 5 is detected by the sample identifier 22, making it possible to determine whether what has been deposited on the biological sample measuring sensor 3 is a blood sample or a control liquid, on the basis of the information stored in the control/blood determination data storage memory 25.

With this embodiment, a computation formula corresponding to the determination result is selected from the computation formula storage memory 27 on the basis of this determination result, the blood glucose level or other such measurement result is calculated with this computation formula, and the final measurement result is displayed on the display section 2.

Switching Control by Amplifiers 14 and 15

The switching control performed by the amplifiers 14 and 15 in the biological sample measuring device of this embodiment will now be described.

With the biological sample measuring device of this embodiment, before the type of biological sample is identified as discussed above, the amplifier 14 or 15 to be used is selected according to whether the voltage value (see FIG. 5) outputted from the amplifier 14 connected in the initial measurement state is above or below a threshold (such as 125 mV). The vertical axis maximum value Vx in the graph shown in FIG. 5 is 22.5 mV, for example.

More specifically, when the output value at point α shown in FIG. 5 is compared with a threshold (125 mV), the output value at point α is below the threshold (point α in FIG. 5 corresponds to point α in FIG. 4). Therefore, the controller 20 changes the switch 16 shown in FIG. 3 from on to off on the basis of the determination result of the threshold determination section 21, and closes the switch 17, changing it from off to on. As a result, the switch 17 is closed and the output of the current-voltage converter 13 is connected to the A/D converter 18 via the amplifier 15. Specifically, the graph in FIG. 5 shows the characteristics when the amplifier 15 has been selected, whose degree of amplification is greater than that of the amplifier 14.

The graph in FIG. 5 shows the characteristics when various kinds of biological sample measurement were performed in a living space (such as a place at 25° C.). That is, in this embodiment, if the output value from the biological sample measuring sensor 3 is below the specific threshold even in a room-temperature environment such as this, more accurate measurement can be performed by amplifying the output value.

Figure 6:
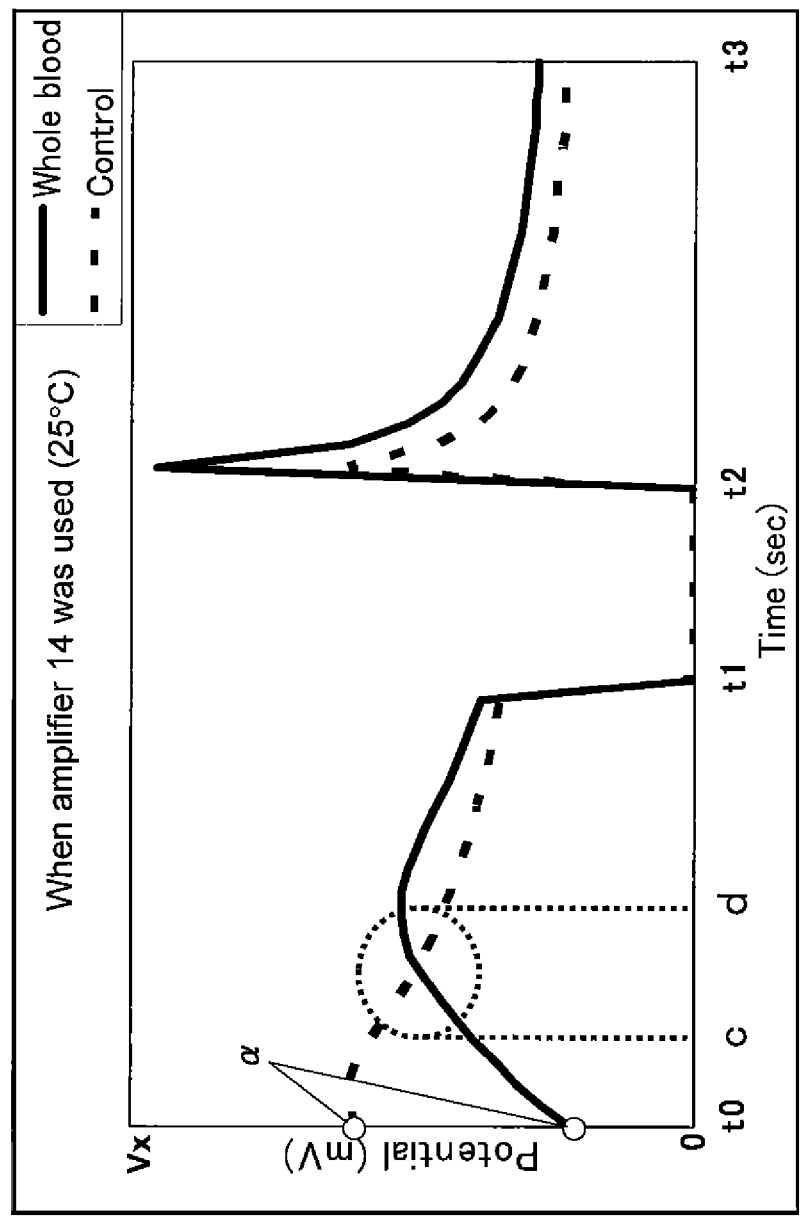
FIG. 6 is a comparative graph of the operating waveform diagram of FIG. 5.

As a comparative example of the graph shown in FIG. 5, the results are also given for amplification processing using the amplifier 14 set to a normal degree of amplification even when the output value in the same room-temperature environment (the output value at point α in the drawing) is below a specific threshold (125 mV). Here, the vertical axis maximum value Vx in the graph shown in FIG. 6 is 5.6 mV, for example. In this case, although the same waveform appears as that in FIG. 5, the measurement range is narrower in FIG. 6 (0 to 5.6 mV) than in FIG. 5 (0 to 22.5 mV). Thus, as mentioned above, more accurate measurement can be accomplished by performing amplification processing using the amplifier 15, which has a greater degree of amplification, when the output value is low, even in a room-temperature environment.

Figure 7:
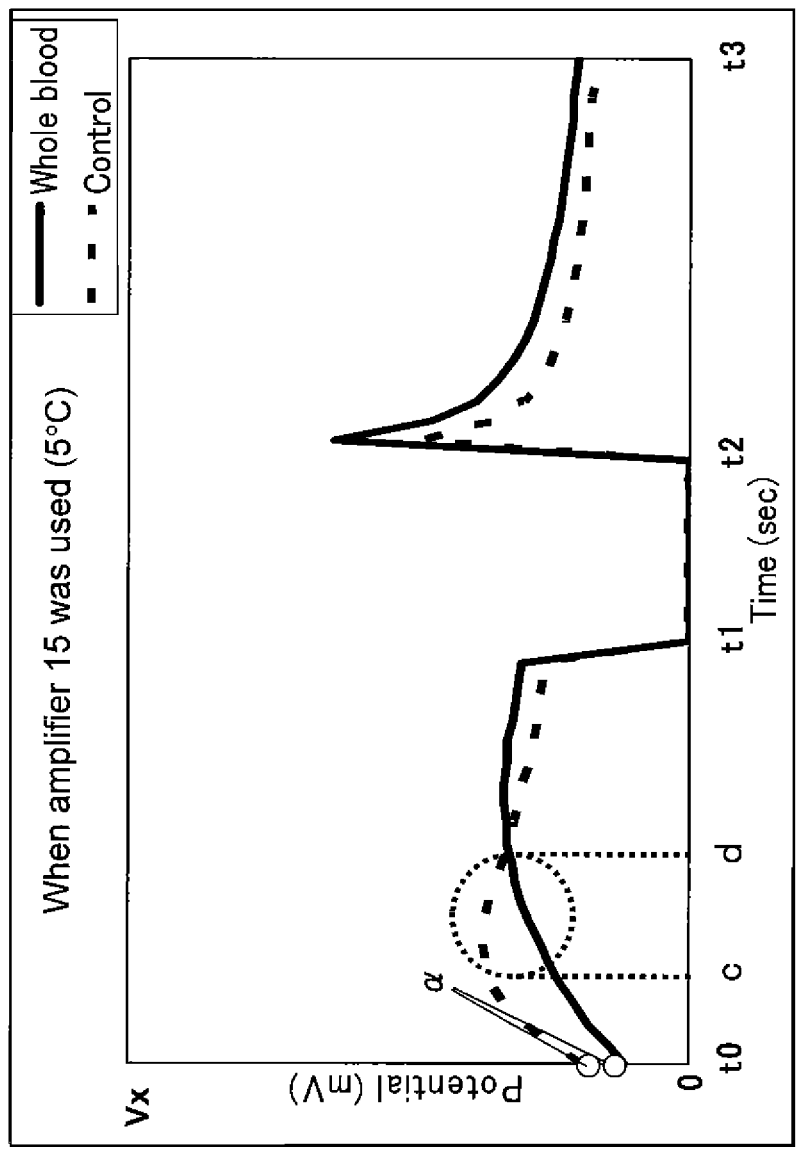
FIG. 7 is an operating waveform diagram in a low-temperature environment for the biological sample measuring device of FIG. 1.

In contrast, the graph in FIG. 7 shows the measurement result in a low-temperature environment of 5° C. The vertical axis maximum value Vx in the graph shown in FIG. 7 is 0.7 mV, for example. As is easy to see from a comparison of FIGS. 7 and 5, the output value is smaller in a low-temperature environment, but the characteristics of the blood sample and the control liquid between c and d on the time axis appear the same as in FIG. 5.

However, in a low-temperature environment of 5° C., the reaction is generally slower, and the level of the output signal also tends to be correspondingly lower. Accordingly, the signal is the same as at 25° C. (shown in FIG. 5), but at 5° C. (FIG. 7) the rise is slower and the value is smaller at the initial time from t0, both with the control liquid and blood.

The reason for setting a condition of 5° C. as the low-temperature environment is that the measurement range for a biological sample measuring device is generally set to between 5 and 45° C., and the lower limit thereof is 5° C.

Specifically, just as in the graph shown in FIG. 7, with a blood sample the value rises continuously between c and d on the time axis, and conversely, with a control liquid, the value falls continuously between c and d on the time axis.

Figure 8:
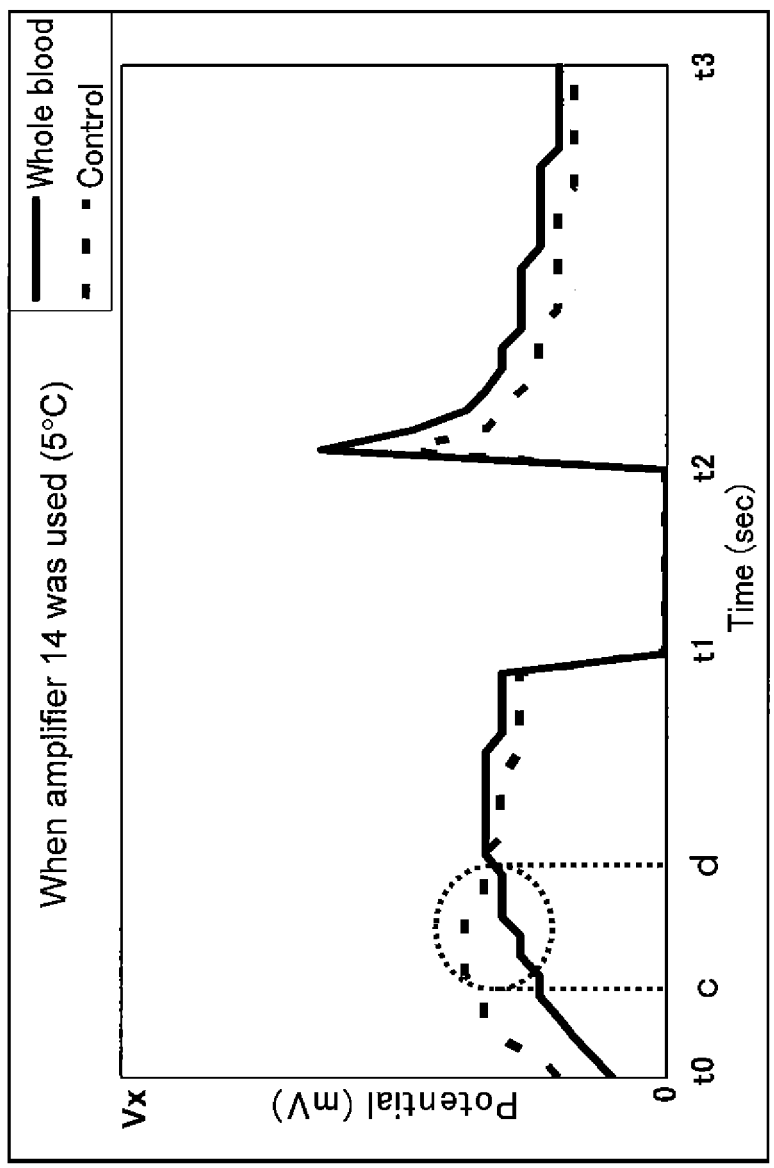
FIG. 8 is a comparative graph of the operating waveform diagram of FIG. 7.
Figure 10:
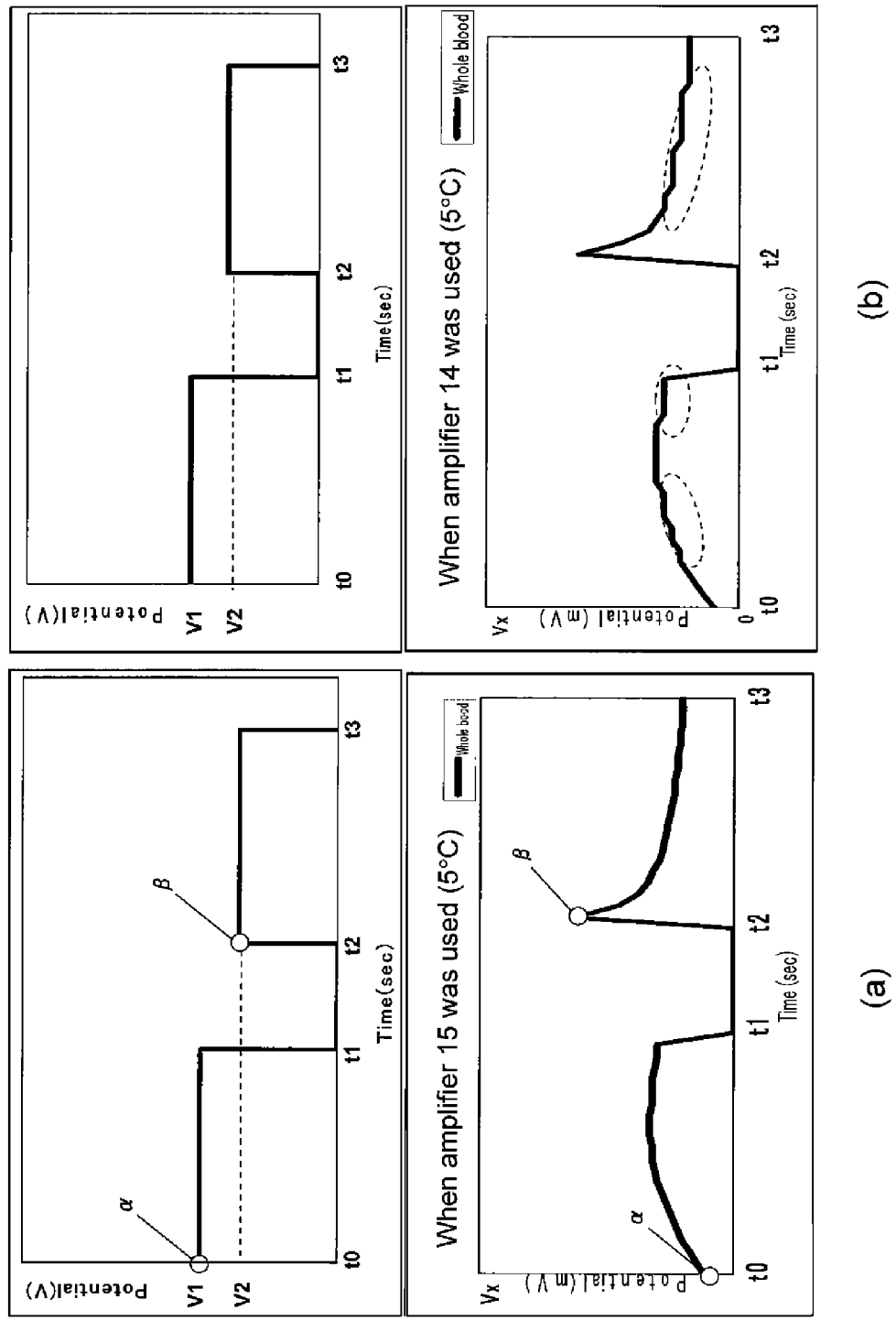
FIG. 10a is a graph of the voltage pattern applied in the biological sample measuring device pertaining to another embodiment of the present invention, and of the output result of amplification processing.
FIG. 10b shows the output result thereof.
Figure 11:
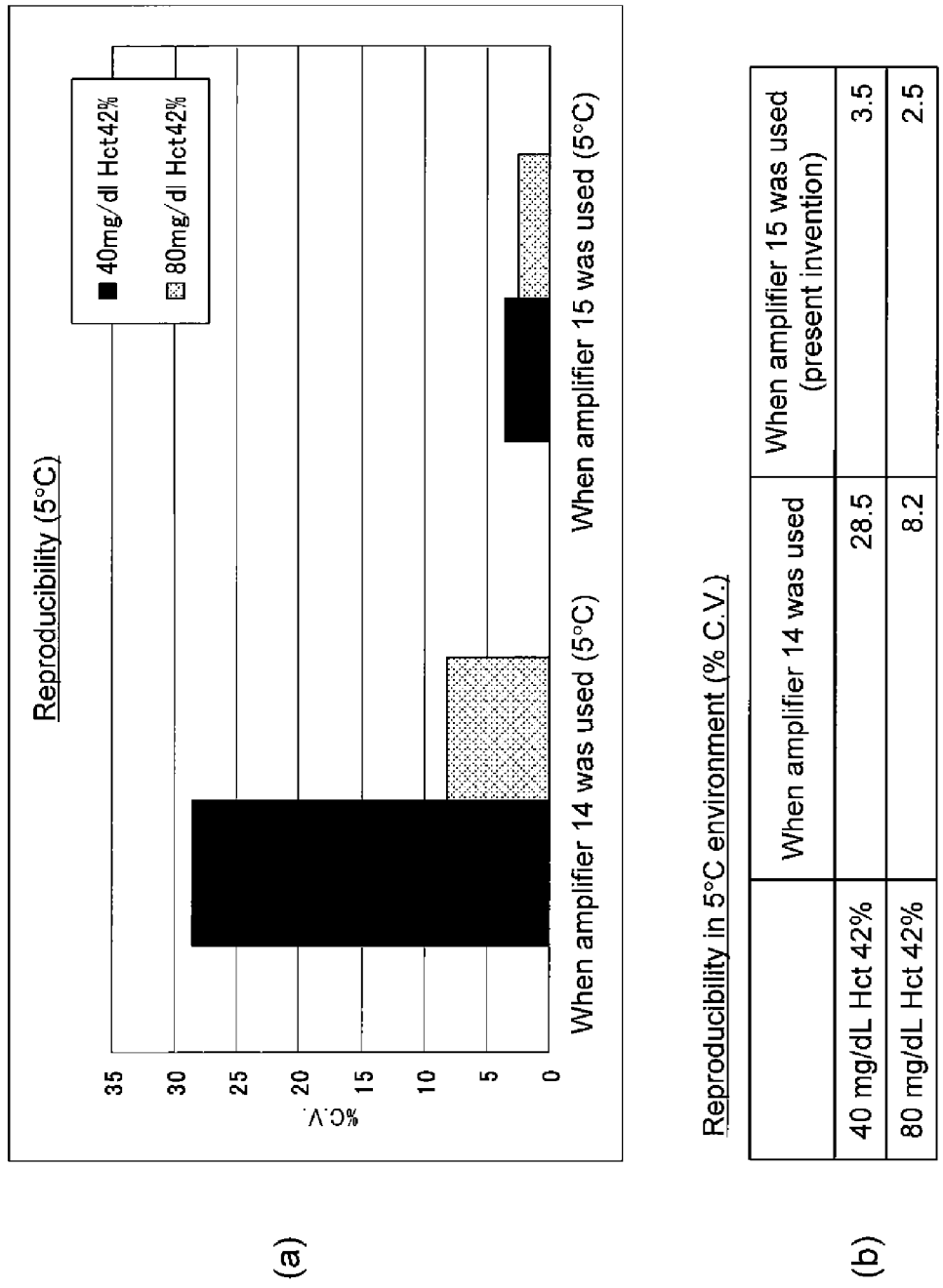
FIG. 11a is a graph of reproducibility in a low-temperature environment when measuring glucose concentration with the biological sample measuring device of FIG. 1.
FIG. 11b is a table of the results of comparing this reproducibility.

Next, FIG. 8 is a graph of the output value in amplification processing using the amplifier 14, which has a lower degree of amplification in a low-temperature environment. The vertical axis maximum value Vx in the graph shown in FIG. 8 is 0.7 mV, for example. In measurement in a low-temperature environment, when amplification processing is performed using the same amplifier 14 as in a room-temperature environment, as shown in FIG. 8, the blood and control liquid do not both rise and fall smoothly between c and d on the time axis of the graph, and instead exhibit characteristics of moving up and down in a jerky fashion.

Specifically, during measurement in a low-temperature environment, the output current from the working electrode 9 is smaller than in a room-temperature environment, so with the amplifier 14 set to a normal degree of amplification, output to the A/D converter 18 is impossible at an adequate input level. Accordingly, as shown in FIG. 8, limitations on the resolution of the A/D converter 18 end up creating a jagged waveform. As a result, with the output shown in FIG. 8, type identification cannot be performed by the sample identifier 22, and proper measurement cannot be carried out.

In view of this, with the biological sample measuring device of this embodiment, the amplifier 15, which is set to a greater degree of amplification than the amplifier 14, is selected and used even in measurement in a low-temperature environment, so the characteristics of a blood sample and a control liquid can be detected more accurately, as shown in FIG. 7. Thus, the sample identifier 22 can make the proper identification, and detection accuracy in a low-temperature environment can be improved over that in the past.

FIGS. 9a and 9b show the verified results for the identification of a blood sample and a control liquid in a low-temperature environment (5° C.), for detection accuracy by switching control of the above-mentioned amplifiers 14 and 15.

As shown in FIG. 9a, when the amplifier 14 is used, which has a lower degree of amplification in a low-temperature environment, it can be seen that the number of times the control liquid was mistaken for a blood sample was 5 out of 1500, and the number of times the blood sample was mistaken for the control liquid was 1 out of 4000.

On the other hand, if as a result of the above-mentioned threshold determination the amplifier being used is switched to the amplifier 15, then as shown in FIG. 9b, it can be seen that the number of times the control liquid and the blood sample were mistaken for each other was zero for both.

It is clear from the above results that a blood sample and a control liquid can both be accurately identified with the biological sample measuring device in this embodiment, and it can be seen that this is particularly effective in an environment in which the sensor output value is small, such as in a low-temperature environment.

Furthermore, with the biological sample measuring device in this embodiment, even in something other than a low-temperature environment, the above configuration increases the input signal level and therefore increases the S/N ratio and improves measurement accuracy.

Embodiment 2

The biological sample measuring device pertaining to another embodiment of the present invention will be described through reference to FIGS. 10a to 11b.

With the biological sample measuring device in this embodiment, the switching of the amplifiers 14 and 15 described in Embodiment 1 is applied to the normal measurement of glucose concentration.

In this embodiment, the same voltage pattern as in Embodiment 1 above, which is applied during glucose measurement in a low-temperature environment (5° C.), is applied from the voltage application section 12 to the counter electrode 8, and the output results compared when using the amplifier 14 and the amplifier 15. The biological sample measuring device in this embodiment has the same configuration as the biological sample measuring device in Embodiment 1 above, and will be described using the same label numbers.

The upper rank in FIGS. 10a and 10b is graphs of the same voltage application pattern as in Embodiment 1 above, and the lower rank is graphs of the results (current values) outputted using the amplifier 15 and the amplifier 14. The vertical axis maximum values Vx in the graphs shown in FIGS. 10a and 10b are 0.7 mV, for example.

Specifically, in this embodiment, just as in Embodiment 1 above, the voltage V1 is applied for the time t0-t1, the voltage V2 is applied for the time t2-t3, and the glucose concentration is measured using the measurement values obtained at one or more points within the application time. The above-mentioned specific voltages V1 and V2 are, for example, from 0.05 to 1 V, preferably 0.1 to 0.8 V, and more preferably 0.2 to 0.5 V.

With the biological sample measuring device in this embodiment, as shown in the lower graph in FIG. 10a, when the amplifier 15 was used, which had the higher degree of amplification, the output results for the time t0-t1 and for the time t2-t3 both form a smooth curve. Consequently, the glucose concentration can be accurately calculated on the basis of the output results.

Meanwhile, as shown in the lower graph in FIG. 10b, when the amplifier 14 was used, which had the lower degree of amplification, the output results for the time t0-t1 and for the time t2-t3 both form a curve that is jagged in places. Consequently, the glucose concentration can not be accurately calculated.

As discussed above, if the result of applying the voltages (V1 and V2) in the specific voltage application pattern is that the resulting output result is small, there is the risk that glucose concentration cannot be measured accurately if the amplifier 14 connected at the start of measurement is used. Accordingly, with the biological sample measuring device in this embodiment, the output values at points α and β in FIG. 10a are compared with a specific threshold, and if the output value from the amplifier 14 connected to the working electrode 9 in the initial state is below the specific threshold (25 mV here), the amplifier 15 with the higher degree of amplification is used. The controller 20 at this point changes the switch 16 to its OFF state, and changes the switch 17 to its ON state (see FIG. 3).

Consequently, the output result from the working electrode 9 is subjected to amplification processing by raising the degree of amplification with the amplifier 15 over that of the amplifier 14, and the graph shown in the lower half of FIG. 10a is obtained. As a result, even when the output value from the biological sample measuring sensor 3 is low in a low-temperature environment, resolution can be increased and more accurate glucose measurement can be performed than in the past by switching the amplifiers 14 and 15 in stages.

FIGS. 11a and 11b show the verified results using blood samples of different glucose concentrations in a low-temperature environment (5° C.) for reproducibility as a result of switching the amplifiers 14 and 15 as mentioned above. Two different blood samples were used, whose glucose concentrations and Hct values were 40 mg/dL and 42% for sample A, and 80 mg/dL and 42% for sample B.

As a result, as shown in FIGS. 11a and 11b, even in a low-temperature environment, just as in a normal situation, when the amplifier 14 with the lower degree of amplification is used, it can be seen that there is extremely great variance between sample A (reproducibility of 28.5%) and sample B (reproducibility of 8.2%). The reason for this seems to be that when the amplifier 14 is used in a low-temperature environment, as shown in FIG. 8, the output value results in jagged curve on the graph, so an accurate measurement value cannot be calculated.

Meanwhile, if the result of the above threshold determination is to switch the amplifier 14 and the amplifier 15, and use the amplifier 15 with the higher degree of amplification, it can be seen that the variance is far lower than when using the amplifier 14, with a reproducibility of 3.5% with sample A and 2.5% with sample B.

The above results tell us that with the biological sample measuring device in this embodiment, it is clear that an accurate and stable measurement result is obtained regardless of how much the glucose concentration increases or decreases, and this is particularly effective in measurement of low sensor output values, such as in a low-temperature environment.

Furthermore, with the biological sample measuring device in this embodiment, even in something other than a low-temperature environment, the above configuration increases the input signal level and therefore increases the S/N ratio and improves measurement accuracy.

Embodiment 3

The biological sample measuring device pertaining to yet another embodiment of the present invention will be described through reference to FIGS. 12a and 12b.

The biological sample measuring device in this embodiment differs in that the voltage is applied in a different voltage application pattern from that in Embodiments 1 and 2 above, and hematocrit (Hct) is measured in addition to the glucose concentration.

Figure 12:
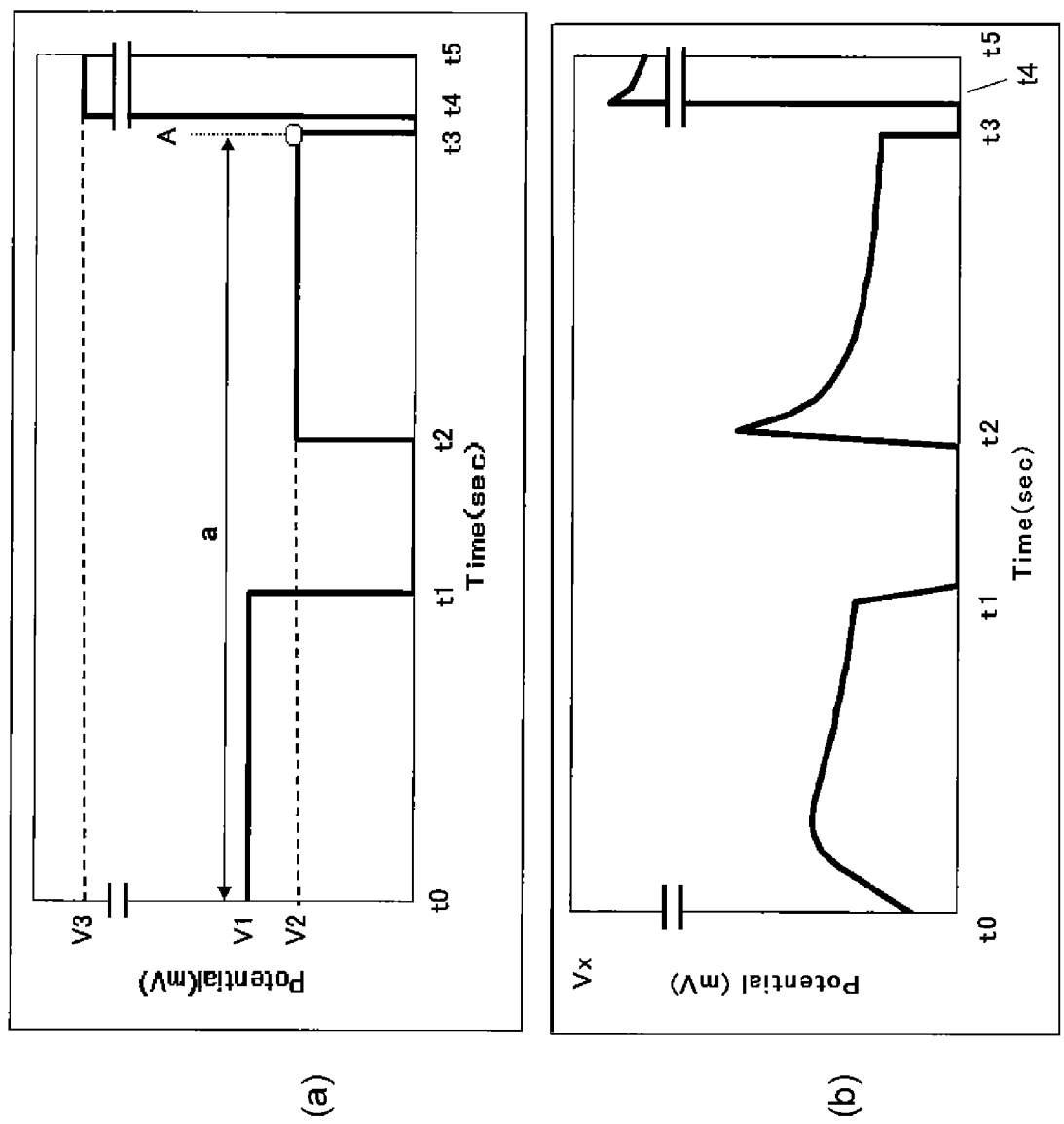
FIG. 12a is a graph of the voltage pattern applied in the biological sample measuring device pertaining to yet another embodiment of the present invention.
FIG. 12b is a graph of the output result thereof.

As shown in FIG. 12a, in this embodiment, just as in Embodiments 1 and 2 above, the pre-application voltage V1 is applied prior to measurement for the time t0-t1, the voltage V2 for measuring glucose is applied for the time t2-t3, and the glucose concentration is measured at the time t3. Furthermore, in this embodiment, in addition to the above-mentioned voltages, a voltage V3 for measuring Hct is applied for a time t4-t5. The voltage V3 is preferably from 1 to 10 V, and more preferably 1 to 6.5 V.

When the maximum output of the A/D converter 18 during the period a shown in FIG. 12a is set to an output voltage value of 100 mV, for example, as shown in FIG. 12b, the maximum output of the A/D converter 18 at point A is set to an output voltage value of 25 mV, for example, and the maximum output of the A/D converter 18 during the period b is set to an output voltage value of 266.7 mV, for example, the measurement resolution during the period a is 0.0132 mV, the measurement resolution at point A is 0.0033 mV, and the measurement resolution during the period b is 0.018 mV. That is, the ratio of these outputs is A:a:b≈1:4:11.

These output current values and the attendant measurement resolutions are just examples, and are not limited to the values discussed above. Also, the output ratio may be A:a:b=1:4:8, A:a:b=1:3:12, or the like.

With the biological sample measuring device in this embodiment, when the voltage application pattern shown in FIG. 12A is employed, and the output value from the amplifier 14 is lower than a specific threshold, the system switches to use of the amplifier 15, which allows glucose concentration to be measured very accurately just as in Embodiment 2 above, and also allows Hct to be measured.

Embodiment 4

The biological sample measuring device pertaining to yet another embodiment of the present invention will be described through reference to FIGS. 13a and 13b.

The biological sample measuring device in this embodiment differs from the above embodiments in a voltage application pattern for detecting the deposit of a blood sample is added at a stage prior to the start of glucose measurement. The present invention is not limited to control for performing threshold determination by using a voltage application pattern for deposit detection as in this embodiment, and threshold determination may be performed by using a voltage application pattern for determination.

Figure 13:
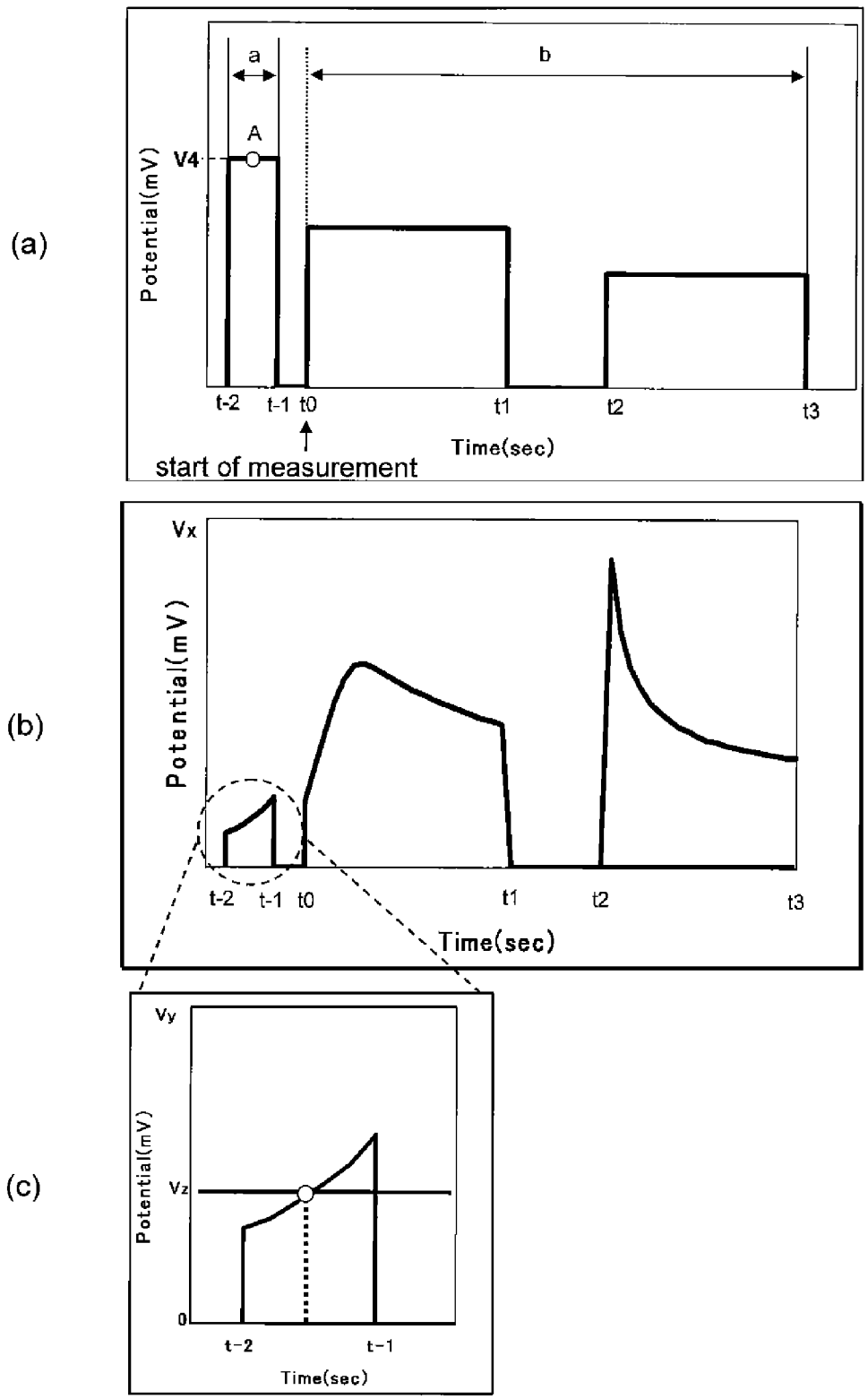
FIG. 13a is a graph of the voltage application pattern applied in the biological sample measuring device pertaining to yet another embodiment of the present invention.
FIG. 13b is a graph of the output result thereof.
FIG. 13c is a graph of when the threshold is determined.

Specifically, with this embodiment, as shown in FIG. 13a, a specific voltage V4 is applied during the period (t-2)-(t-1) prior to the glucose concentration measurement starting point t0. The voltage V4 here is, for example, from 0.05 to 1 V, and preferably 0.1 to 0.8 V.

This specific voltage V4 during the period (t-2)-(t-1) has been applied in the past in order to detect whether or not a blood sample has been deposited on the biological sample measuring sensor 3, and in this embodiment, the output result of this applied voltage for sample detection is used to control the switching of the amplifiers 14 and 15 (range switching control).

More specifically, the output result for the applied voltage V4 used for sample detection has the curved waveform shown in FIG. 13b. Here, the vertical axis maximum value Vx in the graph shown in FIG. 13b is 30 mV, for example. Thus, with this embodiment, as shown in FIG. 13c, the output value Vz located in the middle of the period (t-2)-(t-1) (4.5 mV, for example, in this embodiment) is compared with a specific threshold stored in the memory 23 to determine whether or not to switch the amplifiers 14 and 15 (range switching control).

Here, if the output value Vz (4.5 mV, for example, in this embodiment) is greater than the specific threshold stored in the memory 23, it is concluded to be unnecessary to further amplify the output value, and the connection with the amplifier 14 is left as it is. On the other hand, if the output value Vz is less than that specific threshold, the connection is switched form the amplifier 14 to the amplifier 15, which yields an output with a higher degree of amplification.

By thus performing threshold determination by utilizing the voltage applied prior to the start of measurement of glucose concentration, and switching the amplifiers 14 and 15 according to this result, resolution can be improved and more accurate measurement carried out, even in an environment of a low output value, such as low-temperature environment, as discussed above.

Furthermore, with the biological sample measuring device of this embodiment, even in something other than a low-temperature environment, the above configuration increases the input signal level and therefore increases the S/N ratio and improves measurement accuracy.

Other Embodiments

An embodiment of the present invention was described above, but the present invention is not limited to or by the above embodiment, and various modifications are possible without departing from the gist of the invention.

(A)

In the above embodiment, The determination section 19 (threshold determination section 21) for performing threshold determination, and the controller 20 that selected one of the switches 16 and 17 were described as separate control blocks, but the present invention is not limited to this.

For example, the configuration may be such that a single controller performs both threshold determination and the selection of the switches 16 and 17.

Alternatively, the configuration may be such that threshold determination is performed in a control block such as a determination section formed inside a controller.

(B)

In the above embodiment, an example was described in which the current value outputted from the working electrode 9 of the biological sample measuring sensor 3 was converted into a voltage value by the current-voltage converter 13, and amplification processing was performed by either of the amplifiers 14 and 15, but the present invention is not limited to this.

For example, amplification processing may be performed using the current value, without first converting to a voltage value.

(C)

In the above embodiment, an example was described in which amplification processing was performed by selectively using the two amplifiers 14 and 15 according to the magnitude of the output value from the working electrode 9 of the biological sample measuring sensor 3, but the present invention is not limited to this.

Figure 14:
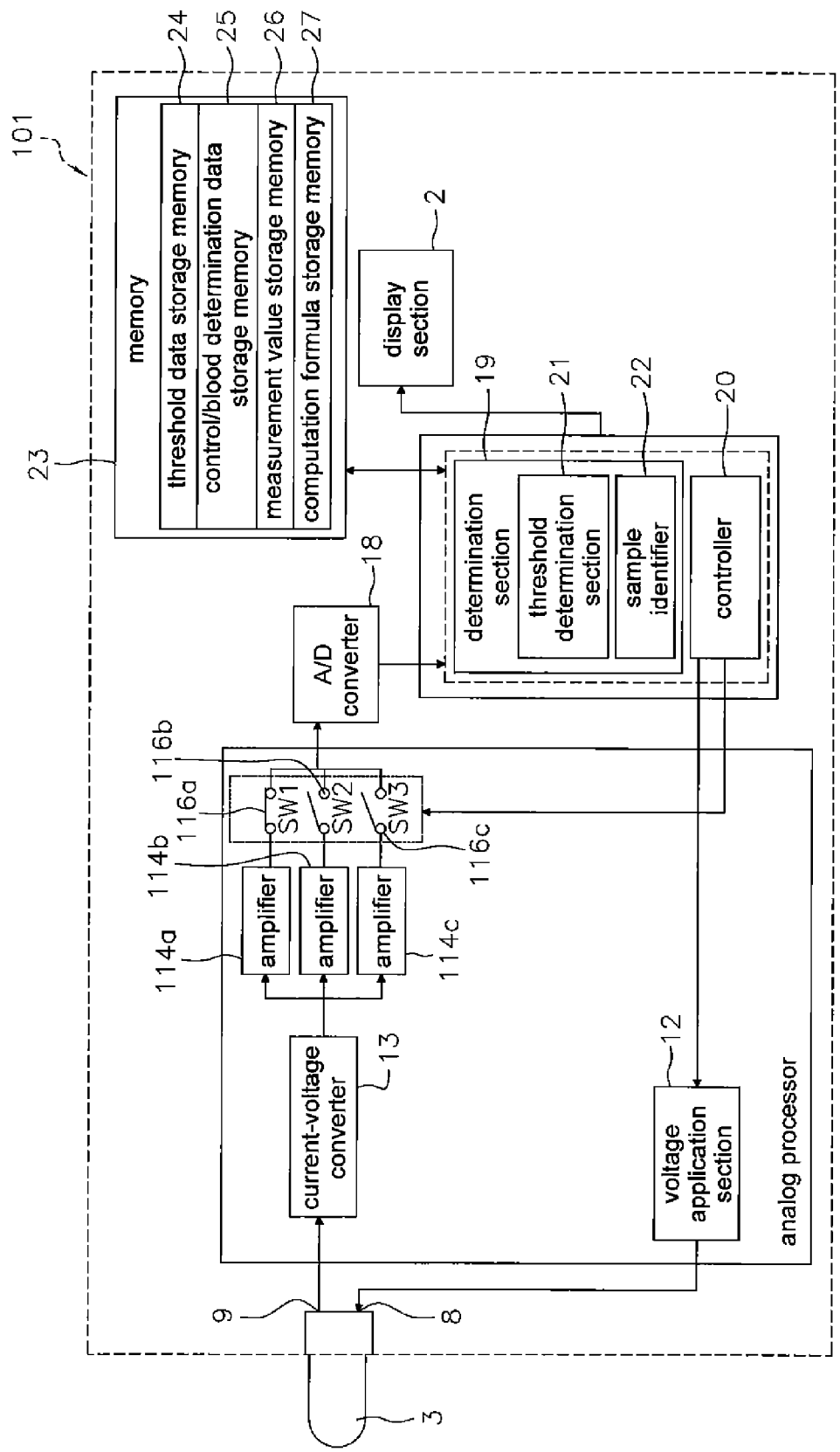
FIG. 14 is a control block diagram of the biological sample measuring device pertaining to yet another embodiment of the present invention.

For example, as shown in FIG. 14, the amplifier that performs amplification processing may be a biological sample measuring device 101 provided with three amplifiers 114a, 114b, and 114c. Alternatively, the biological sample measuring device may be provided with more than three amplifiers.

In this case, the degree of amplification can be switched in three stages, such as ×1, ×4, and ×6, by switching switches 116a, 116b, and 116c on or off according to the size of the output from the biological sample measuring sensor.

Also, in the control block diagram in FIG. 14, the amplifiers 114a, 114b, and 114c may be switched continuously at specific intervals, and the output values at the switched amplifiers stored in the memory.

In this case, the optimal output value data stored in the memory is selected on the basis of the temperature data at the time of measurement, the initial output value data, and so forth upon completion of measurement, and the result is used as correct data. After this, correction or other such computation is performed, and the measurement result is displayed on the display section 2 as a measurement value.

The specific interval here should be within a range of 0.01 to 0.5 second, and preferably a range of 0.01 to 0.1 second. The same processing can be carried out when two amplifiers are provided.

(D)

In the above embodiment, an example was described in which threshold determination by the threshold determination section 21 was performed on the basis of a signal (digital voltage value) received from the A/D converter 18, but the present invention is not limited to this.

For example, the output value from the working electrode 9 that will be the object of threshold determination is not limited to the above-mentioned digital voltage value, and may instead be a current value from before conversion by the current-voltage converter 13, or an analog value from before A/D conversion by the A/D converter 18.

(E)

In the above embodiment, an example was described in which the types of blood sample and control liquid were identified by the sample identifier 22 formed inside the determination section 19, but the present invention is not limited to this.

For example, even with biological samples other than those mentioned above, the type of each biological sample may be determined by detecting properties unique to that biological sample.

(F)

In the above embodiment, an example was described in which determination of the type of biological sample and control liquid was performed on the basis of the change in the voltage value between c and d on the time axis in the graph shown in FIG. 5, but the present invention is not limited to this.

For example, the type of biological sample deposited on the biological sample measuring sensor may be determined by making use of the technology discussed in Patent Literature 1.

More specifically, with a sensor system for quantifying the concentration of a substance in a sample by measuring current, the ratio between the measured current value and the time differential of this current value is used as a sample discrimination parameter, and a discrimination function is defined in which the discrimination parameter serves as an independent variable, for identifying the types of a plurality of samples to be analyzed. The value of the discrimination parameter is plugged into this discrimination function, the resulting numerical value is used as a discrimination index, and the type of sample, that is, whether it is blood or a control liquid, is determined on the basis of this discrimination index.

This discrimination method is similar to the above embodiment in that it allows the types of biological sample and control liquid to be identified.

(G)

In the above embodiment, an example was described in which measurement was performed by applying a specific voltage from the voltage application section 12 to the biological sample measuring sensor 3, but the present invention is not limited to this.

Figure 15:
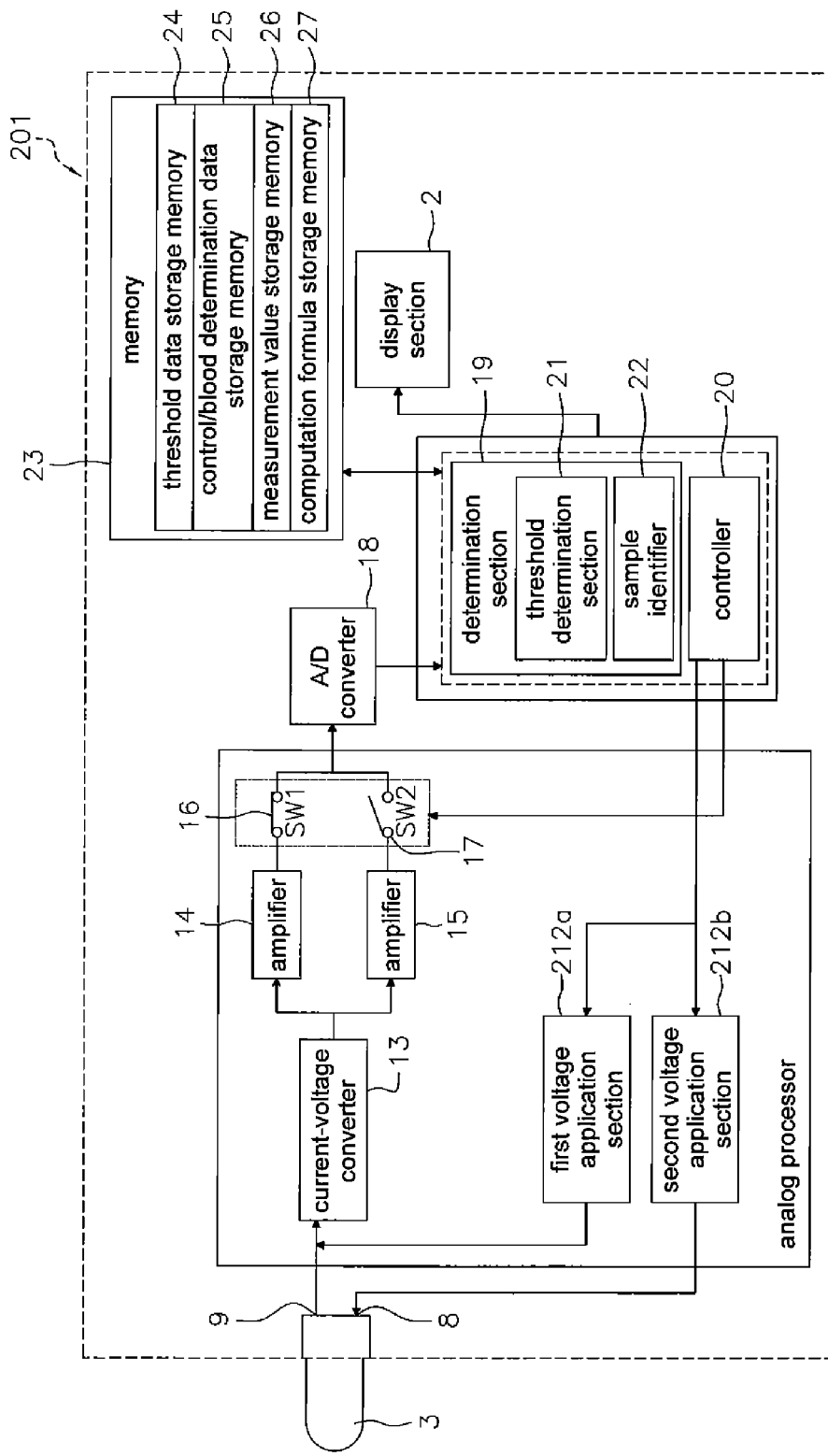
FIG. 15 is a control block diagram of the biological sample measuring device pertaining to yet another embodiment of the present invention.

For example, as shown in FIG. 15, a biological sample measuring device 201 may be provided with a first voltage application section 212a and a second voltage application section 212b.

In this case, voltage is applied from the first voltage application section 212a to the biological sample measuring sensor 3, and a reference voltage is applied from the second voltage application section 212b to a terminal serving as the counter electrode of the biological sample measuring sensor 3. At this point the voltage applied to both ends of the biological sample measuring sensor 3 is the voltage applied from the first voltage application section 212a minus the voltage applied from the second voltage application section 212b. The current that flows when voltage is applied to both ends of the biological sample measuring sensor 3 is converted into voltage by the current-voltage converter 13. Then, in order to make the voltage suitable for the A/D converter 18, the voltage is amplified by the amplifier 14 or the amplifier 15 and inputted to the A/D converter 18.

(H)

In the above embodiment, an example was described in which amplification processing was performed by selectively using the two amplifiers 14 and 15 according to the magnitude of the output value from the working electrode 9 of the biological sample measuring sensor 3, but the present invention is not limited to this.

Figure 16:
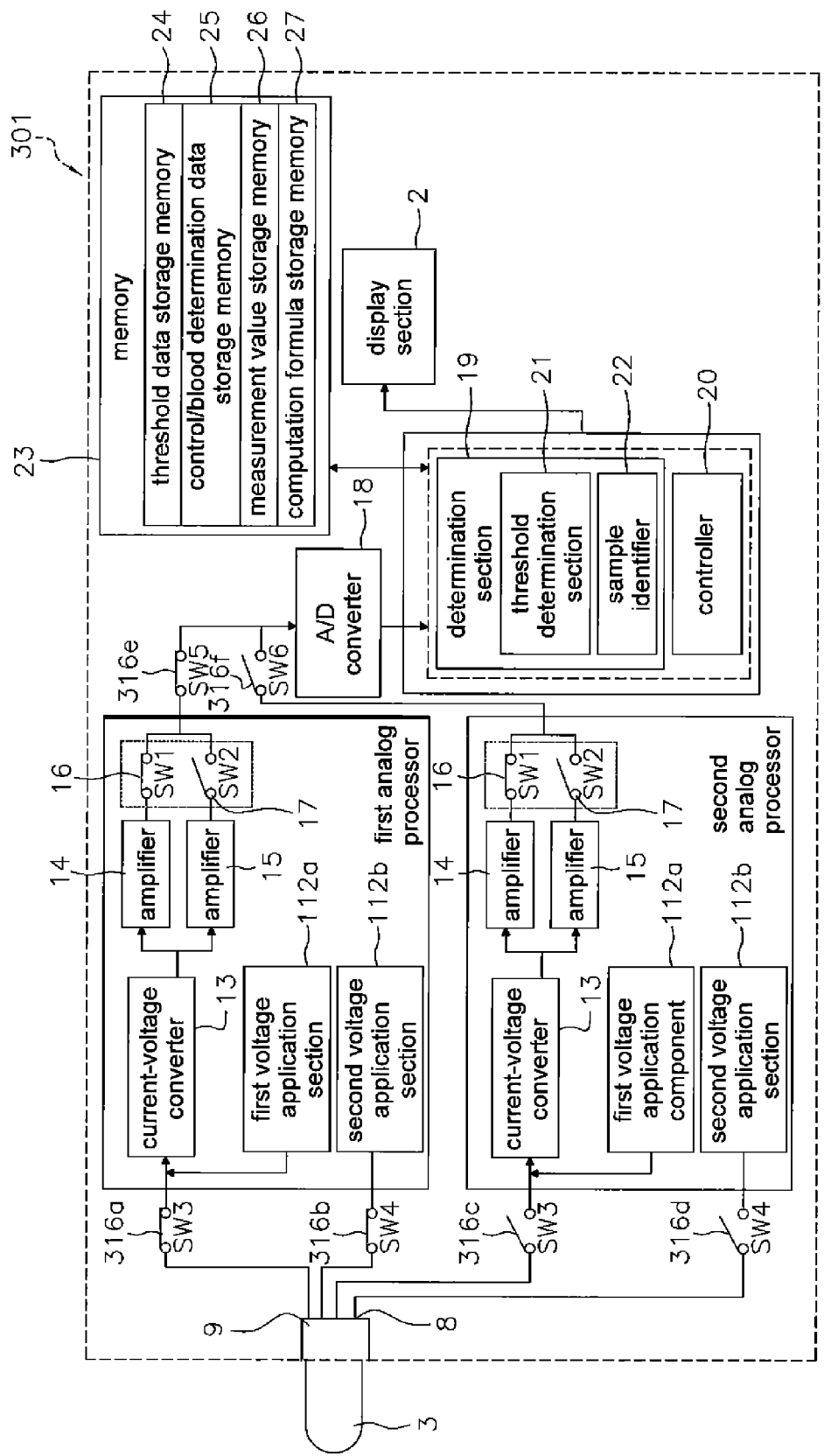
FIG. 16 is a control block diagram of the biological sample measuring device pertaining to yet another embodiment of the present invention.

For example, when a combination of a plurality of electrodes is used for the biological sample measuring sensor, or when voltage is to be applied to a plurality of electrodes at the same time, first and second analog processors having the same configuration may be provided, and the entire analog processing is switched, as with the biological sample measuring device 301 shown in FIG. 16.

In this case, voltage can be applied from the first analog processor by switching on a switch 316a and a switch 316b. Furthermore, voltage can be applied from the second analog processor by switching on a switch 316c and a switch 316d. Also, the output from either the first analog processor or the second analog processor can be inputted to the A/D converter 18 and subjected to A/D conversion by switching on either a switch 316e or a switch 316f.

In the example shown in FIG. 16, two amplifiers are provided inside each analog processor, but just one may be provided instead. In this case, the switches SW1 and SW2 are unnecessary.

With the biological sample measuring device shown in FIG. 16 and the above embodiment, an example was given in which the switches 316a and 316b and the switches 316c and 316d were connected individually to connecting electrodes 8 and 9, etc., of the sensor 3, but the present invention is not limited to this.

For example, the switch 316a and the switch 316c may be connected to the same connecting electrode (such as just the connecting electrode 9), or the switch 316b and the switch 316d may be connected to the same connecting electrode (such as just the connecting electrode 8).

(I)

In the above embodiment, an example was described in which a single current-voltage converter 13 was provided, but the present invention is not limited to this.

Figure 17:
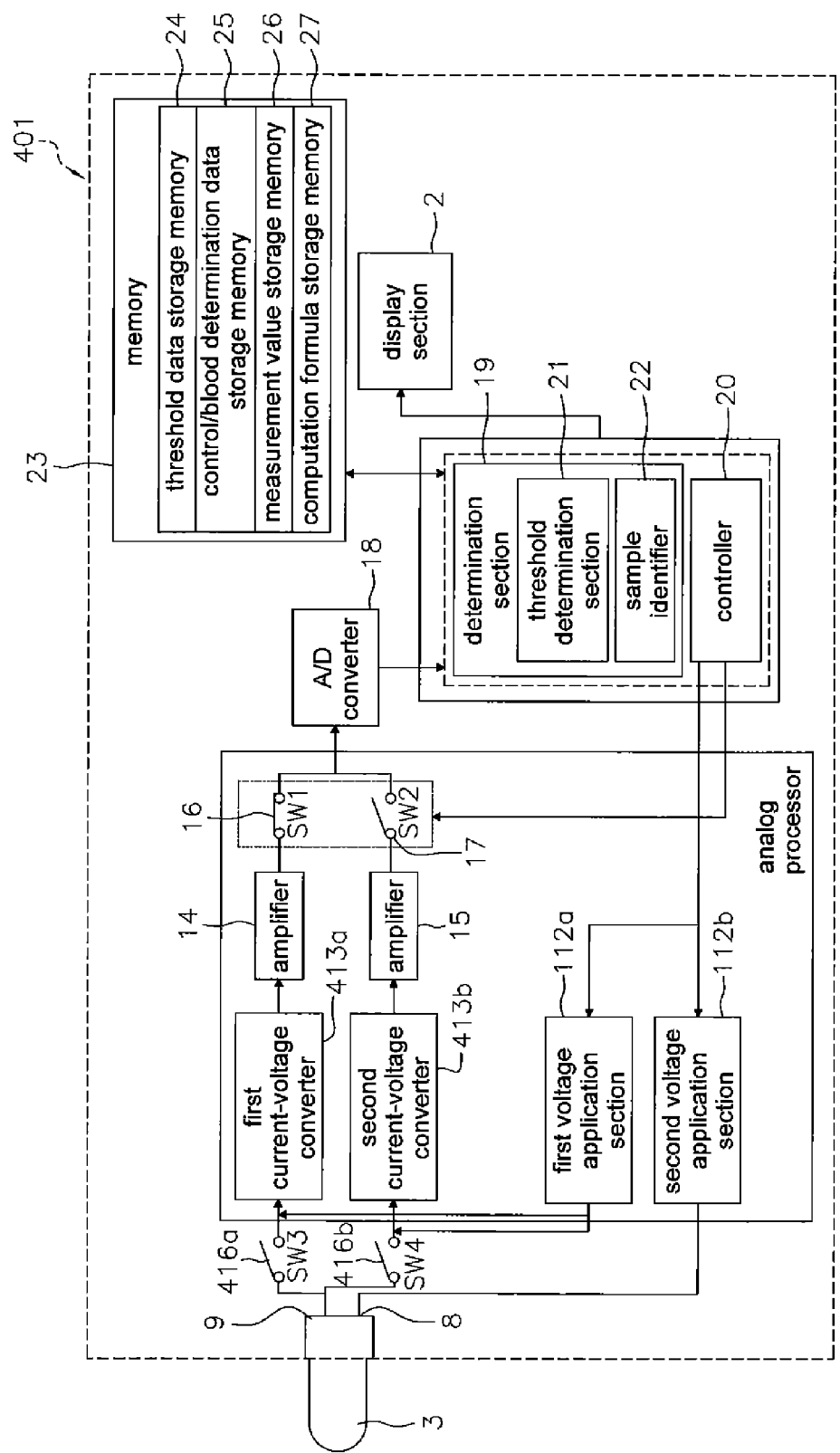
FIG. 17 is a control block diagram of the biological sample measuring device pertaining to yet another embodiment of the present invention.

For example, as shown in FIG. 17, a biological sample measuring device 401 may comprise two current-voltage converters (first and second current-voltage converters 413a and 413b).

In this case, the amplifiers 14 and 15 are provided one each to the first and second current-voltage converters 413a and 413b, respectively, and which amplifier is used is switched with this configuration.

That is, with the configuration shown in FIG. 17, a current-voltage converter and an amplifier make a set, and two of these sets (a first current-voltage converter 413a with the amplifier 14, and a second current-voltage converter 413b with the amplifier 15) are provided. Thus, in switching the amplifier 14 or 15 to be used, control may be performed so that the switch 16 and a switch 416a, or the switch 17 and a switch 416b are synchronously switched, respectively.

(J)

In the above embodiment, an example was described in which amplification processing was performed by selectively using the two amplifiers 14 and 15 according to the magnitude of the output value from the working electrode 9 of the biological sample measuring sensor 3, but the present invention is not limited to this.

Figure 18:
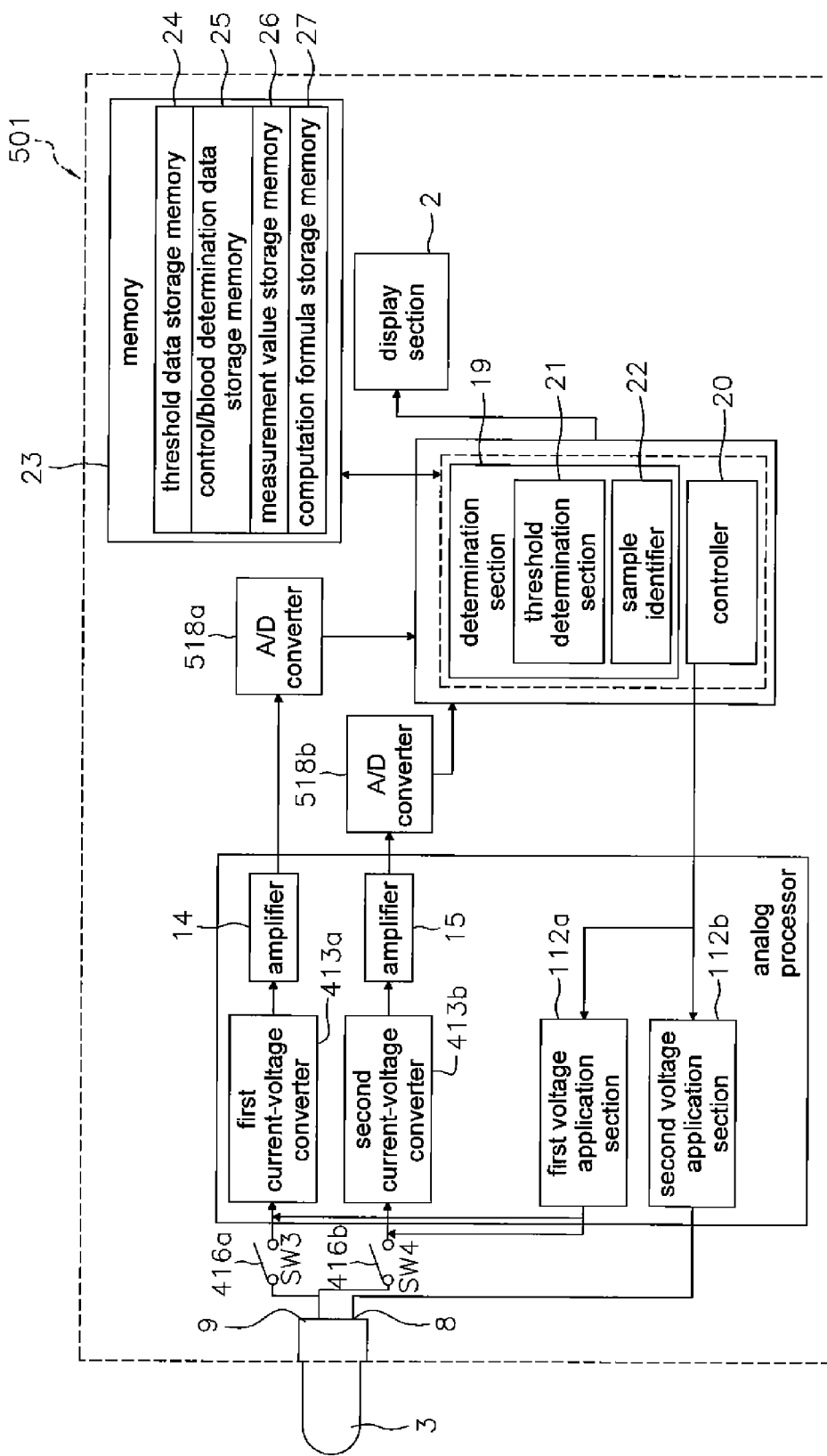
FIG. 18 is a control block diagram of the biological sample measuring device pertaining to yet another embodiment of the present invention.

For example, as shown in FIG. 18, a biological sample measuring device 501 may comprise two groups of current-voltage converters (first and second current-voltage converters 413a and 413b), amplifiers (amplifiers 14 and 15), and A/D converters (A/D converters 518a and 518b).

In this case, the current-voltage converters, amplifiers, and A/D converters disposed in two groups can be used to switch the entire system. Furthermore, since the A/D converters are each disposed to the rear of the respective amplifier, data can be acquired simultaneously from two circuits.

(K)

In the above embodiment, an example was described in which amplification processing was performed by selectively using the two amplifiers 14 and 15 according to the magnitude of the output value from the working electrode 9 of the biological sample measuring sensor 3, but the present invention is not limited to this.

Figure 19:
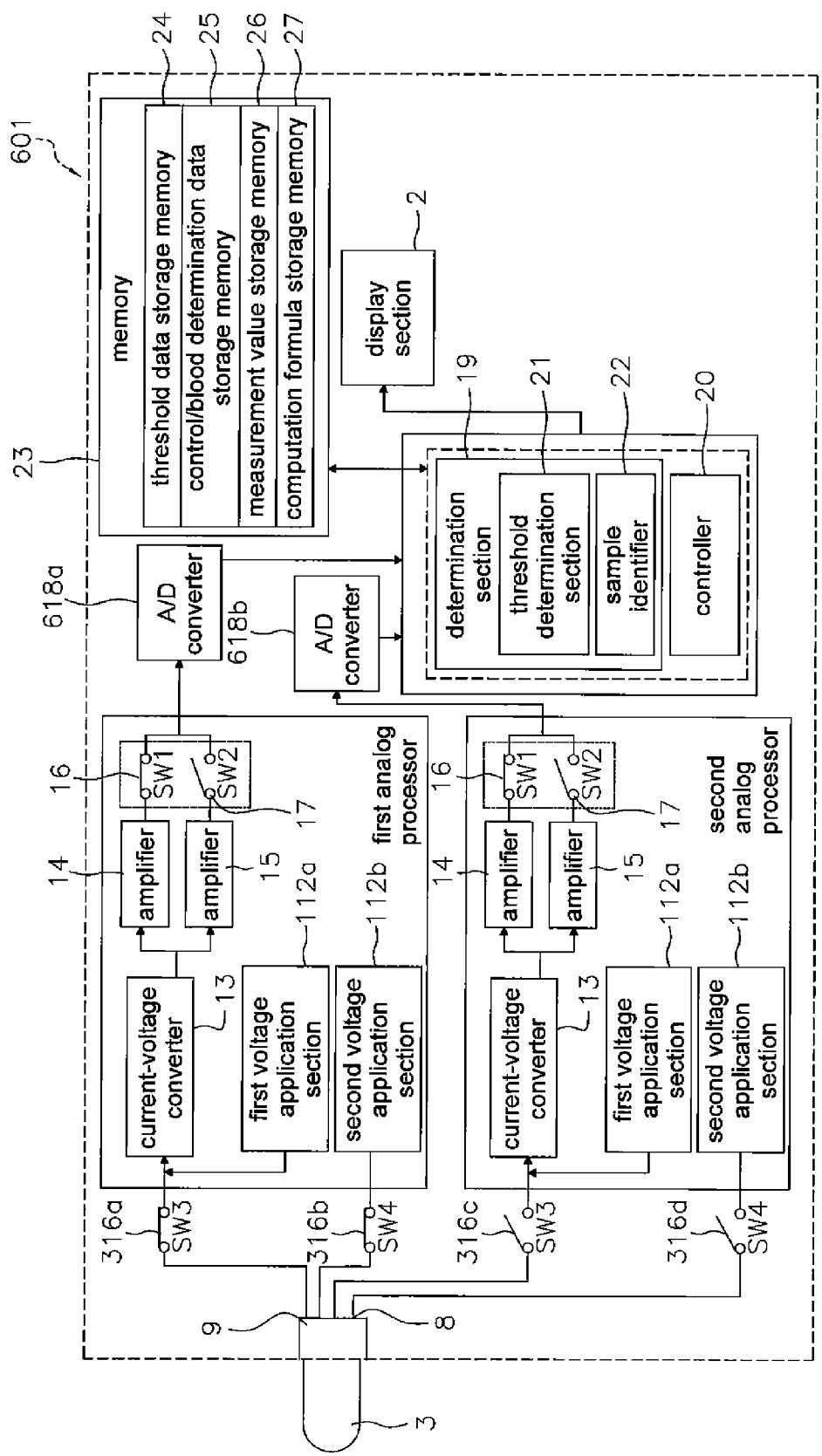
FIG. 19 is a control block diagram of the biological sample measuring device pertaining to yet another embodiment of the present invention.

For example, as shown in FIG. 19, a biological sample measuring device 601 may comprise A/D converters 618a and 618b to the rear of the above-mentioned first analog processor and second analog processor, respectively.

In this case, since two circuits are provided up to the A/D converters 618a and 618b, voltage can be applied simultaneously at two locations, and A/D conversion can be performed simultaneously.

In the example shown in FIG. 19, there are two amplifiers inside each of the analog processors, but the configuration may instead be such that there is just one amplifier in each. In this case, the switches SW1 and SW2 are unnecessary.

Just as in the other embodiment (H) discussed above, since there is no need to switch the voltage applied to the biological sample measuring sensor 3, the switching-use switches 316a and 316b are also unnecessary on the sensor side of the analog processor.

With the configuration shown in FIG. 19 and the above embodiment, an example was given in which the switches 316a, 316b, 316c, and 316d were connected individually to connecting electrodes 8 and 9, etc., of the sensor 3, but the present invention is not limited to this.

For example, the switch 316a and the switch 316c may be connected to the same connecting electrode (such as just the connecting electrode 9), or the switch 316b and the switch 316d may be connected to the same connecting electrode (such as just the connecting electrode 8).

(L)

In the above embodiment, an example was described in which threshold determination, determination of the type of biological sample, concentration measurement, and so forth were carried out by the determination section 19, while selective switching of the amplifiers was carried out by the controller 20, but the present invention is not limited to this. For example, threshold determination, determination of the type of biological sample, concentration measurement, and so forth may be processed within a single function block. Alternatively, the processing of each may be carried out in three or more function blocks.

(M)

In the above embodiment, an example was described in which the timing at which the plurality of amplifiers with different degrees of amplification (the amplifiers 14 and 15, etc.) were switched was at the start of voltage application, but the present invention is not limited to this.

For example, the timing at which the plurality of amplifiers with different degrees of amplification are switched may be at any point during voltage application.

(N)

In the above embodiment, an example was described in which amplification processing was performed by selectively using the two amplifiers 14 and 15 disposed in a parallel relation according to the magnitude of the output value from the working electrode 9 of the biological sample measuring sensor 3, but the present invention is not limited to this.

Figure 20:
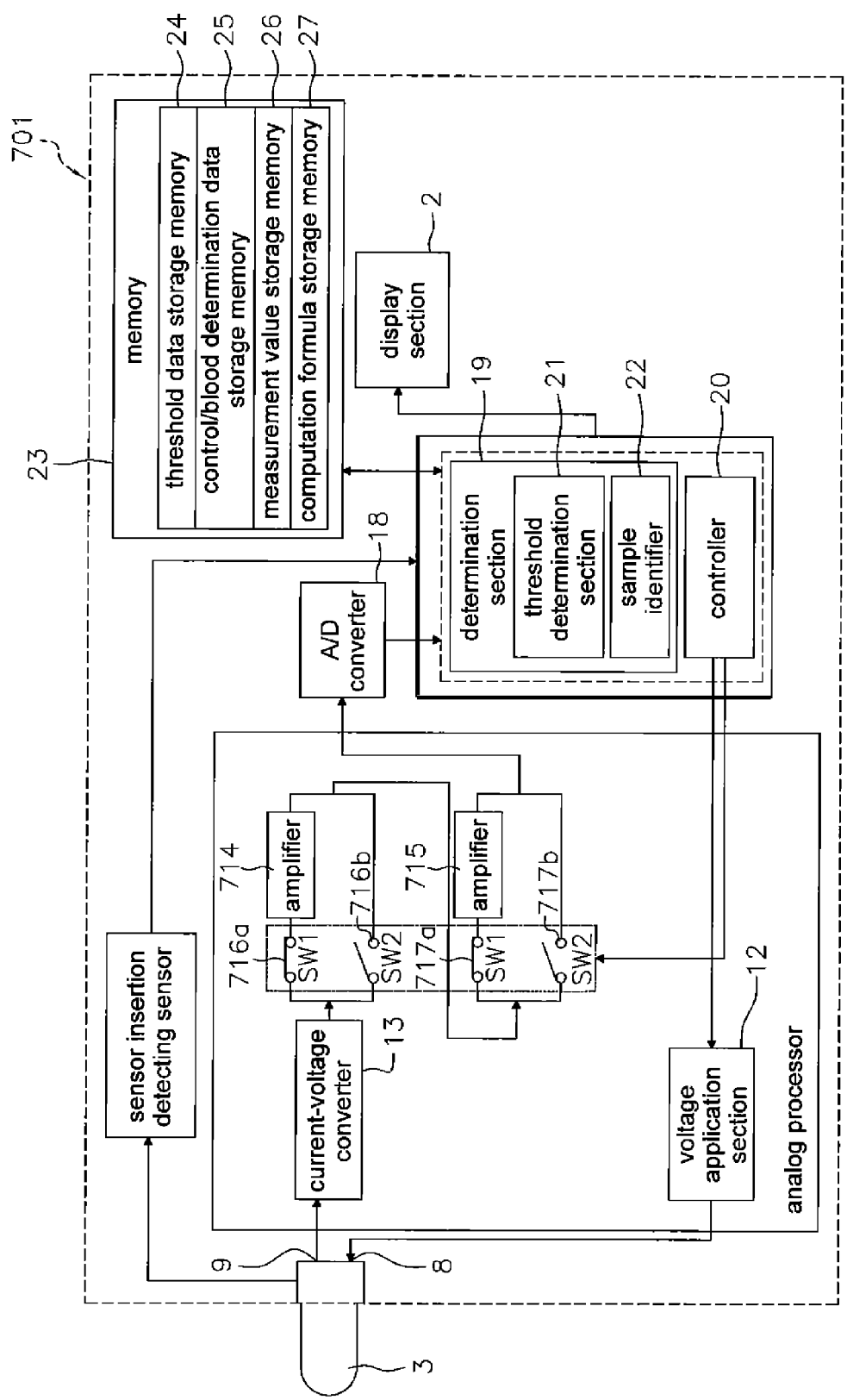
FIG. 20 is a control block diagram of the biological sample measuring device pertaining to yet another embodiment of the present invention.

For example, as shown in FIG. 20, a biological sample measuring device 701 may be capable of selectively using amplifiers 714 and 715 by connecting two amplifiers 714 and 715 in series, switching switches 716a and 716b used for the amplifier 714 and disposed on the upstream side, and switching switches 717a and 717b used for the amplifier 715 and disposed on the downstream side.

INDUSTRIAL APPLICABILITY

With the biological sample measuring device of the present invention, the output signal from the working electrode is smaller during measurement in a low-temperature environment, so the accuracy of measuring blood glucose levels, etc., in a low-temperature environment can be increased over that in the past by selecting the output of a second amplifier whose degree of amplification is the higher of first and second amplifiers, which means that the present invention can be widely applied to biological sample measuring devices that measure blood glucose level and other such biological information.

REFERENCE SIGNS LIST 1 main body case
2 display section
3 biological sample measuring sensor
4 mounting portion
5 substrate
6 spacer
7 cover
8 counter electrode
9 working electrode
10 reagent
11 groove
12 voltage application section
13 current-voltage converter
14 amplifier (first amplifier)
15 amplifier (second amplifier)
16 switch
17 switch
18 A/D converter
19 determination section (controller)
20 controller (controller)
21 threshold determination section
22 sample identifier
23 memory
24 threshold data storage memory
25 control/blood data storage memory
26 measurement value storage memory
27 computation formula storage memory
101 biological sample measuring device
114a to 114c amplifiers (first and second amplifiers)
116a to 116c switches
201 biological sample measuring device
212a first voltage application section
212b second voltage application section
301 biological sample measuring device
316a to 316b switches
401 biological sample measuring device
413a to 413b current-voltage converters
501 biological sample measuring device
601 biological sample measuring device
701 biological sample measuring device
714, 715 amplifier
716a, 716b switch
717a, 717b switch

The invention claimed is:

1. A biological sample measuring device, comprising:
a mounting portion to which is mounted a biological sample measuring sensor, said biological sample measuring sensor having an electrode section including at least a working electrode and a counter electrode, and a reagent provided on the electrode section, wherein a biological sample is deposited on the biological sample measuring sensor and reacts with the reagent;
a voltage application section that applies voltage to the electrode section of the biological sample measuring sensor mounted to the mounting portion;
a current-voltage converter connected to the working electrode of the biological sample measuring sensor;
a first amplifier connected to the current-voltage converter, the first amplifier being configured to amplify a signal outputted from the working electrode, and amplify the signal at a first amplitude;
a second amplifier connected to the current-voltage converter, the second amplifier being configured to amplify a signal outputted from the working electrode, and amplify the signal at a second amplitude that is greater than the first amplitude; and
a controller that compares the value of an output result outputted from either the first amplifier or the second amplifier with a preset threshold, and selectively uses either the first amplifier or the second amplifier.

2. The biological sample measuring device according to claim 1,
wherein the controller determines the type of biological sample on the basis of the output result outputted from either the first amplifier or the second amplifier.

3. The biological sample measuring device according to claim 2,
wherein the controller detects the slope of the output result in a specific time band, and determines whether the biological sample deposited on the biological sample measuring sensor is a blood sample or a control liquid.

4. The biological sample measuring device according to claim 1,
wherein the controller measures the concentration of the biological sample on the basis of the output result outputted from the first amplifier or the second amplifier.

5. The biological sample measuring device according to claim 4,
wherein the controller selects between the first and second amplifiers by comparing the threshold with an output result of a voltage pattern used for biological sample detection and applied prior to measurement of the concentration of the biological sample.

6. A biological sample measuring device, comprising:
a mounting portion to which is mounted a biological sample measuring sensor, said biological sample measuring sensor having an electrode section including at least a working electrode and a counter electrode, and a reagent provided on the electrode section, wherein a biological sample is deposited on the biological sample measuring sensor and reacts with the reagent;
a voltage application section that applies voltage to the electrode section of the biological sample measuring sensor mounted to the mounting portion;
a current-voltage converter connected to the working electrode of the biological sample measuring sensor;
a first amplifier connected to the current-voltage converter, the first amplifier being configured to amplify a signal outputted from the working electrode, and amplify the signal at a first amplitude;
a second amplifier connected to the current-voltage converter, the second amplifier being configured to amplify a signal outputted from the working electrode, and amplify the signal at a second amplitude that is greater than the first amplitude;
a first switch provided at the first amplifier and a second switch provided at the second amplifier such that one of the first amplifier and the second amplifier is prevented from outputting while the other one of the first amplifier and the second amplifier is outputting; and
a controller that compares the value of an output result outputted from either the first amplifier or the second amplifier with a preset threshold, and controls the switch so as to activate either one of the first amplifier or the second amplifier.

\* \* \* \* \*